United States Patent [19]

Sackler et al.

[11] Patent Number: 5,672,360
[45] Date of Patent: *Sep. 30, 1997

[54] METHOD OF TREATING PAIN BY ADMINISTERING 24 HOUR ORAL OPIOID FORMULATIONS

[75] Inventors: Richard S. Sackler, Greenwich; Robert F. Kaiko, Weston; Paul Goldenheim, Wilton, all of Conn.

[73] Assignee: Purdue Pharma, L.P., Norwalk, Conn.

[*] Notice: The term of this patent shall not extend beyond the expiration date of Pat. No. 5,478,577.

[21] Appl. No.: 578,688

[22] PCT Filed: Nov. 22, 1994

[86] PCT No.: PCT/US94/13606

§ 371 Date: Jul. 22, 1996

§ 102(e) Date: Jul. 22, 1996

[87] PCT Pub. No.: WO95/14460

PCT Pub. Date: Jun. 1, 1995

[51] Int. Cl.⁶ .................... A61K 9/16; A61K 9/50
[52] U.S. Cl. .................... 424/490; 424/468; 424/480; 424/494; 424/497
[58] Field of Search .................... 424/490, 494, 424/497, 480, 468; 514/25, 490

[56] References Cited

U.S. PATENT DOCUMENTS

| 3,634,584 | 1/1972 | Poole | 424/21 |
|---|---|---|---|
| 3,845,770 | 11/1974 | Theeuwes et al. | 128/260 |
| 3,870,790 | 3/1975 | Lowey et al. | 424/19 |
| 3,916,899 | 11/1975 | Theeuwes et al. | 128/145.8 |

(List continued on next page.)

FOREIGN PATENT DOCUMENTS

| 9047732 | 7/1990 | Australia. | |
|---|---|---|---|
| 9341654 | 2/1995 | Australia. | |
| 0097523 | 1/1984 | European Pat. Off. | A61K 9/26 |
| 0108218 | 5/1984 | European Pat. Off. | A61K 9/22 |

(List continued on next page.)

OTHER PUBLICATIONS

A protocol for a clinical study entitled "A Randomized, Double–Blind, Parallel–Group Study comparing the Efficacy and Safety of Kapanol® to Ms Contin® in the Management of Patients with Moderate to Severe Cancer Pain" (the Protocol). The date of the Protocol is indicated as Feb. 10, 1992 and it bears CDD No. 14556. The sponsor of the study is indicated to be Faulding Pharmaceuticals, an Australian company.

(List continued on next page.)

*Primary Examiner*—Thurman K. Page
*Assistant Examiner*—William E. Benston, Jr.
*Attorney, Agent, or Firm*—Steinberg, Raskin & Davidson, P.C.

[57] ABSTRACT

Patients are treated with 24-hour oral sustained release opioid formulations which, upon administration, provide an initially rapid opioid absorption such that the minimum effective analgesic concentration of the opioid is more quickly achieved. These sustained release opioid formulations include an effective amount of at least one retardant material to cause said opioid analgesic to be released at a such a rate as to provide an analgesic effect after oral administration to a human patient for at least about 24 hours, and are characterized by providing an absorption half-life from 1 to about 8 hours. A method of titrating a human patient utilizing these sustained release opioid formulations is also disclosed.

14 Claims, 14 Drawing Sheets

U.S. PATENT DOCUMENTS

| | | | |
|---|---|---|---|
| 4,377,568 | 3/1983 | Chopra | 424/31 |
| 4,385,078 | 5/1983 | Onda et al. | 427/3 |
| 4,389,393 | 6/1983 | Schor et al. | 424/19 |
| 4,483,847 | 11/1984 | Augart | 424/22 |
| 4,520,172 | 5/1985 | Lehmann et al. | 525/369 |
| 4,548,990 | 10/1985 | Mueller et al. | 525/123 |
| 4,557,925 | 12/1985 | Lindahl et al. | 424/19 |
| 4,600,645 | 7/1986 | Ghebre-Sellassie et al. | 428/403 |
| 4,708,874 | 11/1987 | De Haan et al. | 424/470 |
| 4,728,513 | 3/1988 | Ventouras | 424/461 |
| 4,797,410 | 1/1989 | El-Fakahany | 514/356 |
| 4,806,337 | 2/1989 | Snipes et al. | 71/65 |
| 4,828,836 | 5/1989 | Elger et al. | 424/419 |
| 4,834,984 | 5/1989 | Goldie et al. | 424/488 |
| 4,834,985 | 5/1989 | Elger et al. | 424/488 |
| 4,844,907 | 7/1989 | Elger et al. | 424/465 |
| 4,844,909 | 7/1989 | Goldie et al. | 424/480 |
| 4,861,598 | 8/1989 | Oshlack | 424/468 |
| 4,970,075 | 11/1990 | Oshlack | 424/451 |
| 4,983,730 | 1/1991 | Domeshek et al. | 536/69 |
| 4,990,341 | 2/1991 | Goldie et al. | 424/484 |
| 5,024,842 | 6/1991 | Edgren et al. | 424/473 |
| 5,071,646 | 12/1991 | Malkowska et al. | 424/497 |
| 5,122,384 | 6/1992 | Paradissis et al. | 424/451 |
| 5,133,974 | 7/1992 | Paradissis et al. | 424/480 |
| 5,169,645 | 12/1992 | Shukla et al. | 424/499 |
| 5,202,128 | 4/1993 | Morella et al. | 424/469 |
| 5,266,331 | 11/1993 | Oshlack et al. | 424/468 |
| 5,273,760 | 12/1993 | Oshlack et al. | 424/480 |
| 5,283,065 | 2/1994 | Doyon et al. | 424/467 |
| 5,286,493 | 2/1994 | Oshlack et al. | 424/468 |
| 5,321,012 | 6/1994 | Mayer et al. | 514/25 |
| 5,330,766 | 7/1994 | Morella et al. | 424/490 |
| 5,378,474 | 1/1995 | Morella et al. | 424/469 |
| 5,411,745 | 5/1995 | Oshlack et al. | 424/456 |
| 5,456,923 | 10/1995 | Nakamichi et al. | 424/489 |
| 5,460,826 | 10/1995 | Merrill et al. | 424/470 |
| 5,472,712 | 12/1995 | Oshlack et al. | 424/480 |
| 5,500,227 | 3/1996 | Oshlack et al | 424/476 |
| 5,508,042 | 4/1996 | Oshlack et al. | 424/468 |
| 5,520,931 | 5/1996 | Persson et al. | 424/473 |
| 5,549,912 | 8/1996 | Oshlack et al. | 424/468 |
| 5,580,578 | 12/1996 | Oshlack et al. | 424/468 |
| 5,601,842 | 2/1997 | Bartholomaeus | 424/464 |

FOREIGN PATENT DOCUMENTS

| | | | |
|---|---|---|---|
| 0147780 | 7/1985 | European Pat. Off. | A61K 9/32 |
| 0235986 | 9/1987 | European Pat. Off. | A61K 9/16 |
| 0253104 | 1/1988 | European Pat. Off. | A61K 9/00 |
| 0271193 | 6/1988 | European Pat. Off. | A61K 31/485 |
| 377518A2 | 7/1990 | European Pat. Off. | |
| 0388954 | 9/1990 | European Pat. Off. | A61K 9/14 |
| 0415693 | 3/1991 | European Pat. Off. | A61K 37/02 |
| 0532348 | 3/1993 | European Pat. Off. | A61K 31/135 |
| 0534628 | 3/1993 | European Pat. Off. | A61K 31/485 |
| 0535841 | 4/1993 | European Pat. Off. | A61K 31/485 |
| 0548448 | 6/1993 | European Pat. Off. | A61K 9/50 |
| 0546676 | 6/1993 | European Pat. Off. | A61K 31/60 |
| 0580860 | 2/1994 | European Pat. Off. | A61K 9/14 |
| 0636370 | 6/1994 | European Pat. Off. | A61K 31/485 |
| 0665010 | 8/1995 | European Pat. Off. | A61K 9/26 |
| 377518B1 | 2/1996 | European Pat. Off. | |
| 2178313 | 2/1987 | United Kingdom | A61K 9/14 |
| WO9201446 | 2/1992 | WIPO | A61K 9/50 |
| WO9206679 | 4/1992 | WIPO | A61K 9/16 |
| WO9304675 | 3/1993 | WIPO | A61K 31/16 |
| WO9310765 | 6/1993 | WIPO | A61K 9/22 |
| WO9318753 | 9/1993 | WIPO | A61K 9/16 |
| WO9403161 | 2/1994 | WIPO | A61K 9/52 |
| WO9422431 | 10/1994 | WIPO | A61K 9/20 |
| WO9600066 | 1/1996 | WIPO | A61K 31/485 |
| WO9601629 | 1/1996 | WIPO | A61K 31/485 |
| WO9614058 | 3/1996 | WIPO | A61K 9/14 |

OTHER PUBLICATIONS

Certain Patient Diary Cards, Drug Disposition Records, Case Report Forms and a listing which apparently correlates patient randomization number with the treatment or dosing regiment assigned to each patient.

Patient consent forms, apparently for four study participants.

Certain documents regarding Institutional Review Board Approval for the Faulding–sponsored study.

Investigator Agreements between the study organizers and certain of the principal investigators.

Advertisement:Roxanol SR, ©1988 Roxane Laboratories, Inc.

R. Kaiko and T. Hunt, "Comparison of the Pharmacokinetic Profiles of Two Oral Controlled–Release Morphine Formulations in Healthy Young Adults", Clin. Thera., vol. 13, No. 4, 1991.

R. West and C. Maccarrone, "Single Dose Pharmacokinetics of a New Oral Sustained–Release Morphine Formulation, Kapanol® Capsules", Abstracts—7th World Congress on Pain, Aug. 26, 1993, Abstracts 997–1001.

S. Bloomfield, et al., "Analgesic efficacy and potency of two oral controlled–release morphine preparations", Clin. Pharmacol. Ther., vol. 53, No. 4, pp. 469–478, ©1993.

Advertisement: MS Contin®, ©1986, 1987, The Purdue Frederick Company.

Abraham Sunshine, et al., "Analgesic oral efficacy of tramadol hydrochloride in postoperative pain", *Clin. Pharmacol. Ther.*, Jun. 1992, pp. 740–746.

E. Beubler, "Medikamentose Schmerztherapie: Kriterien, Moglichkeiten, Risken", *Therapiewoche Osterreich*, 7,2 (1992), pp. 90–96, with English translation.

Geoffrey K. Gourlay, Ph.D., et al., "Influence of a high–fat meal on the absorption of morphine from oral solutions", *Clin. Pharmacol. Ther.*, Oct. 1989, pp. 463–468.

Robert Kaiko, et al., "A Single–Dose Study Of The Effect Of Food Ingestion And Timing Of Dose Administration On The Pharmacokinetic Profile Of 30–MG Sustained–Release Morphine Sulfate Tablets", *Current Therapeutic Research*, vol. 47, No. 5, May 1990, pp. 869–878.

Geoffrey K. Gourlay, Ph.D., "The Reproducibility of Bioavailability of Oral Morphine from Solution Under Fed and Fasted Conditions", *Journal of Pain and Sympton Management*, vol. 6, No. 7, Oct. 1991, pp. 431–436.

Robert F. Kaiko, et al., "Controlled–Release Morphine Bioavailability (MS Contin Tablets) in the Presence and Absence of Food", *The Hospice Journal*, vol. 6(4) 1990, pp. 17–30.

N. Yokokawa, et al., "Relationship between plasma concentration of morphine and analgesic effectiveness", *Postgrad Med J*, (1991) 67 (Suppl. 2) pp. 550–554.

Physicians Desk Reference 1994, 48th Edition, pp. 1821–1824.

Abstracts from the Twelfth Annual Congress of the Oncology Nursing Society, May 1987.

J. Lapin et al., "Cancer Pain Management with a Controlled Release Oral Morphine Preparation", Journ. of Pain and Sympton Manag., v 4 (3), pp. 146–151, 1989

J. Lapin et al., "Guidelines for use of Controlled Release Oral Morphine in Cancer Pain Management", Cancer Nursing, v 12 (4), pp. 202–208, 1989.

R.F. Kaiko, "The Pre-and Postoperative Use of Controlled-Release Morphine (MS Contin Tablets):A Review of the Published Literature", Medical Department, The Purdue Frederick Company, Royal Society of Medical Services, International Congress, Symposium Services, No. 149, pp. 147–160 (1989).

H.F. Slowey et al., "Effect of Premedication with Controlled-Release Oral Morphine on Postoperative Pain", Anaesthesia, 1985, vol. 40, pp. 438–440.

MS Contin—Frequency of Daily Dosing, Jan.–Nov. 1990.

R.K. Portenoy, et al., "A Randomized, Double-Blind, Double-Dummy, Crossover Study Comparing the Pharmacokinetics and Pharmacodynamics of Kapanol® Capsules Given Every 24 hours and Every 12 hours with MS Contin® Tablets Given Every 12 Hours in the Management of Patients with Moderate to Severe Chronic Pain".

METHOD OF TREATING PAIN BY ADMINISTERING 24 HOUR ORAL OPIOID FORMULATIONS

The present invention is a U.S. National Phase application of PCT/US94/13606, claiming priority of U.S. Ser. No. 08/156,468, filed Nov. 23, 1993. Priority is also claimed from U.S. Ser. No. 08/086,248, filed Jul. 1, 1993 now abandoned.

BACKGROUND OF THE INVENTION

The present invention relates to bioavailable sustained-release pharmaceutical formulations of analgesia drugs, in particular opioid analgesics, which provide an extended duration of effect when orally administered.

It is the intent of all sustained-release preparations to provide a longer period of pharmacologic response after the administration of the drug than is ordinarily experienced after the administration of the rapid release dosage forms. Such longer periods of response provide for many inherent therapeutic benefits that are not achieved with corresponding short acting, immediate release preparations. This is especially true in the treatment of cancer patients or other patients in need of treatment for the alleviation of moderate to severe pain, where blood levels of an opioid analgesic medicament must be maintained at a therapeutically effective level to provide pain relief. Unless conventional rapid acting drug therapy is carefully administered at frequent intervals to maintain effective steady state blood levels of the drug, peaks and valleys in the blood level of the active drug occur because of the rapid absorption, systemic excretion of the compound and through metabolic inactivation, thereby producing special problems in maintenance of analgesic efficacy.

The prior art teaching of the preparation and use of compositions providing the sustained-release of an active compound from a carrier is basically concerned with the release of the active substance into time psychologic fluid of the alimentary tract. However, it is generally recognized that the mere presence of an active substance in the gastrointestinal fluids does not, by itself, insure bioavailability.

In order to be absorbed, the active drug substance must be in solution. The dissolution time required for a given proportion of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

The primary principle guiding the use of opioid analgesics in the management of chronic pain is the individualization of dosages to meet the different and changing opioid requirements among and within each individual patient. Pain management authorities stress the importance of titration. Titration to the appropriate dose for a particular patient is necessitated by the wide inter-individual differences in the response of different patients to given doses of opioids. While a multitude of factors are responsible for wide inter-individual differences in the response to opioid analgesics, one important factor is rooted in the wide inter-individual variation in metabolism and pharmacokinetics.

Those opioids which are most efficiently titrated are those with relatively short elimination half-lives in the range of 3 to 5 hours (e.g., morphine, hydromorphone, oxycodone) as compared to long (12 to 72 hours) and more variable half-life analgesics(e.g., methadone, levorphanol). The shorter half life drugs approach steady-state concentrations in approximately a day rather than in several days to a week or more. Only at steady-state can one expect that the balance between efficacy and side effects will persist at a given dosing schedule. Having confidence that the patient is at approximate steady-state a day or so following initiation of dosing allows for much quicker assessment of whether the dosage is appropriate for that individual.

Once-a-day orally administrable dosage forms have previously been developed in the art and are commercially available. Presently, however, there are no commercially available sustained-release 24-hour opioid analgesic preparations; however, experience with the 12-hour sustained release preparations have led to a general understanding in the medical community that in order to titrate a patient who is to receive opioid analgesic therapy it is necessary to use an immediate release opioid analgesic dosage form, such as a parenteral formulation, an immediate release solution or tablet, or the like. Only after a suitable steady-state level is achieved in the patient by using immediate release opioid preparations may a patient be switched to a sustained release oral opioid formulation.

It therefore follows that it would be very desirable for practitioners to have available a sustained-release opioid analgesic preparation which provides appropriate pharmacokinetic parameters (e.g., absorption profile) and accompanying pharmacodynamic response in the patient (e.g., relief from pain) such that the same dosage form may be used to both titrate a patient receiving opioid analgesic therapy and used in chronic maintenance therapy after titration of the patient. This would eliminate the need to first titrate a patient on an immediate release opioid dosage form before switching the patient to a sustained-release dosage form for chronic therapy as described above. Preferably the sustained-release preparations will provide a duration of effect lasting longer than about twelve hours such that a drug that may be administered to a patient only once a day. Preferably, the sustained release dosage form will not only provide effective pain relief for a duration of greater than about 12 hours, but will additionally provide a pharmacokinetic and pharmacodynamic profile which will allow a patient who is to receive opioid analgesic therapy to be titrated and chronically treated with the same sustained-release dosage form.

Many of the oral opioid analgesic formulations that are currently available in the market must be administered every four to six hours daily; a selected few are formulated for less frequent 12 hour dosing.

There is also a need to develop a drug formulation which provides an absorption profile which is suitable for both titrating a patient who is receiving opioid analgesic therapy and which also provides sustained release of an opioid analgesic sufficient to provide analgesia for at least about 0.12 hours duration. This would eliminate the need to first titrate a patient with immediate release dosage forms (e.g. parenteral, oral, rectal) of opioid analgesic and then switch the patient to a sustained release form of the opioid analgesic.

Morphine, which is considered to be the prototypic opioid analgesic, has been formulated into twice-daily controlled-release formulations (i.e., MS Contin® tablets, commercially available from Purdue Frederick Company; and Kapanol®, commercially available from F. H. Faulding and Company; and Oramorph® SR, previously referred to as Roxanol® SR, commercially available from Roxane).

An orally administrable opioid formulation which would provide an extended duration of analgesia without higher incidence of adverse effects would be highly desirable. Such an oral sustained-release formulation of an opioid analgesic would be bioavailable and provide effective steady-state blood levels (e.g., plasma levels) of the drug when orally administered such that a duration of analgesic efficacy about 24 hours or more is obtained.

OBJECTS AND SUMMARY OF THE INVENTION

It is accordingly an object of the present invention to provide a method for treating patients in moderate to severe pain with an orally administered pharmaceutical dosage form of an opioid analgesic that is suitable for once-a-day administration.

It is yet another object of the present invention to provide a method for treating patients with a once-a-day opioid analgesic formulation which provides greater analgesic efficacy than that which is obtainable with the preferred Q12H (every 12 hour) analgesic therapies.

It is further an object of the present invention to provide an opioid analgesic dosage form which provides sustained-release of the opioid and is also capable for use in titrating a patient receiving opioid analgesic therapy.

In accordance with the above objects and others, the present invention is related in part to the surprising discovery that in order to provide a 24 hour dosage form of an opioid analgesic, it is critical to formulate a sustained release formulation in pain with an analgesic preparation which provides an initially rapid opioid release so that the minimum effective analgesic concentration can be quickly approached in many patients who have measurable if not significant pain at the time of dosing. Due to the unique release profile of the dosage form of the invention, it is possible to use a single dosage form according to the present invention to titrate a patient receiving opioid analgesic therapy while providing sustained-release of an opioid analgesic to once-a-day sustained release oral dosage opioid formulations which comprise an opioid analgesic and an effective amount of at least one retardant material to cause the opioid analgesic to be released at an effective rate to provide an analgesic effect after oral administration to a human patient for at least about 24 hours.

The inventive formulations, when administered in humans, provide an initially rapid rate of rise in the plasma concentration of the opioid characterized by providing an absorption half-life from 1.5 to about 8 hours. In preferred embodiments, the inventive once-daily oral sustained release formulations provides an absorption half-life from 2 to about 4 hours.

The present invention is also directed to a method for titrating human patients with a sustained release oral opioid formulation. The first step of this method comprises administering to a human patient on a once-a-day basis a unit dose of the inventive once-a-day oral sustained release opioid formulations described above and in the following paragraphs. Thereafter, the method includes the further step of monitoring pharmacokinetic and pharmacodynamic parameters elicited by said formulation in said human patient and determining whether said pharmacokinetic and/or pharmacodynamic parameters are appropriate to treat said patient on a repeated basis. The patient is titrated by adjusting the dose of said opioid analgesic administered to the patient by administering a unit dose of said sustained release opioid analgesic formulation containing a different amount of opioid analgesic if it is determinied that said pharmacokinetic and/or said pharmacodynamic parameters are not satisfactory or maintaining the dose of said opioid analgesic in the unit dose at a previously administered amount if said pharmacokinetic and/or pharmacodynamic parameters are deemed appropriate. The titration is continued by further adjusting the dose of the opioid analgesic until appropriate steady-state pharmacokinetic/pharmacodynamic parameters are acheived in the patient. Thereafter, the administration of the dose of the opioid analgesic in the oral sustained release formulation is continued on a once-a-day basis until treatment is terminated.

The term "bioavailability" is defined for purposes of the present invention as the extent to which the drug (e.g., opioid analgesic) is absorbed from the unit dosage forms.

The term "sustained release" is defined for purposes of the present invention as the release of the drug (e.g., opioid analgesic) at such a rate that blood (e.g., plasma) levels are maintained within the therapeutic range but below toxic levels over a period of time of about 24 hours or longer.

The phrase "rapid rate of rise" with regard to opioid plasma concentration is defined for purposes of the present invention as signifying that the formulation provides a $T_{1/2}$ (abs), or half-life of absorption, from 1.5 about hours to about 8 hours.

The term $T_{1/2}$ (abs) is defined for purposes of the present invention as the amount of time necessary for one-half of the absorbable dose of opioid to be transferred to plasma. This value is calculated as a "true" value (which would take into account the effect of elimination processes), rather than an "apparent" absorption half-life.

The term "steady state" means that a plasma level for a given drug has been achieved and which is maintained with subsequent doses of the drug at a level which is at or above the minimum effective therapeutic level and is below the minimum toxic plasma level for a given drug. For opioid analgesics, the minimum effective therapeutic level will be a partially determined by the amount of pain relief achieved in a given patient. It will be well understood by those skilled in the medical art that pain measurement is highly subjective and great individual variations may occur among patients.

The terms "maintenance therapy" and "chronic therapy" are defined for purposes of the present invention as the drug therapy administered to a patient after a patient is titrated with an opioid analgesic to a steady state as defined above.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
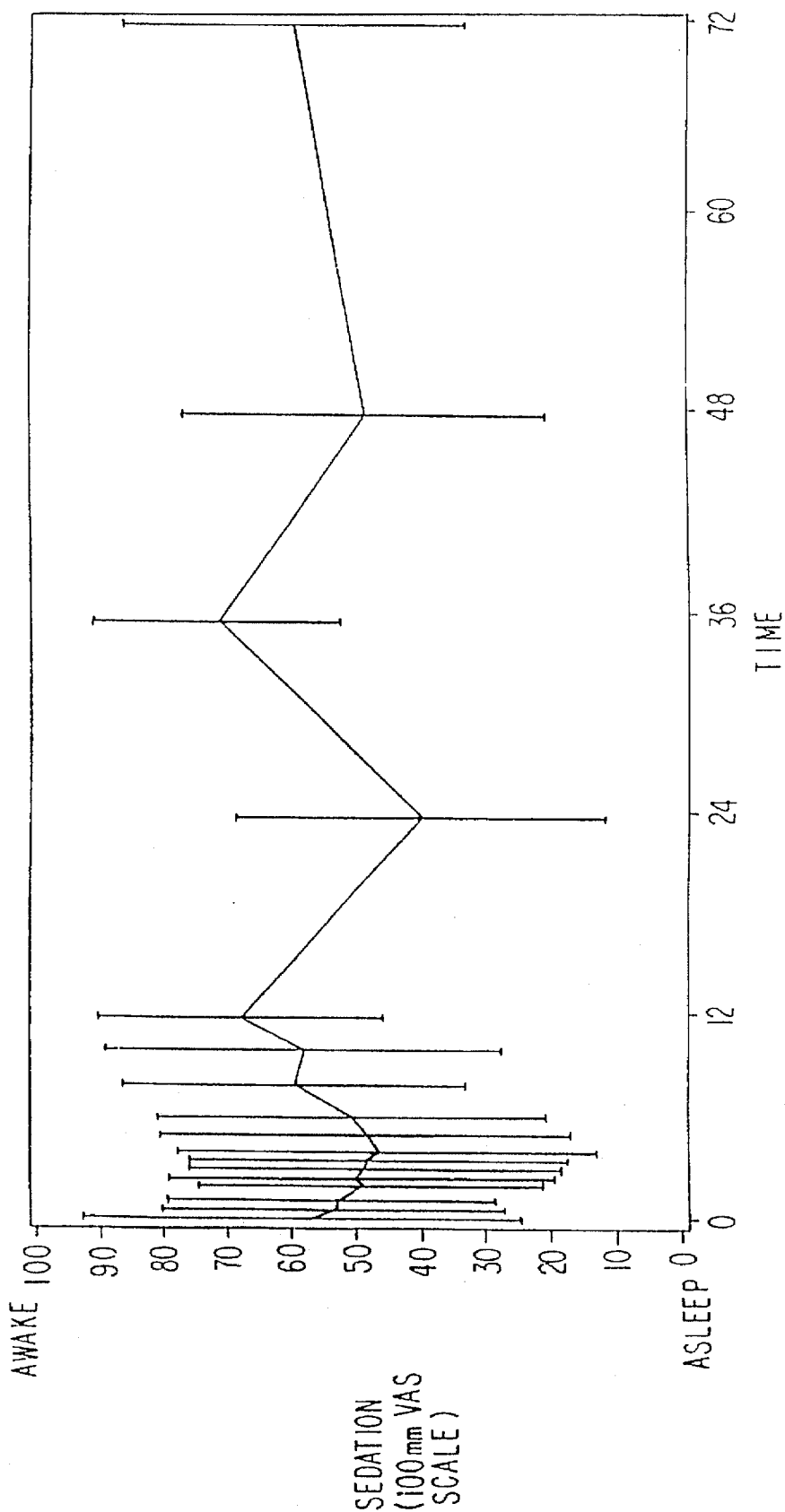
FIG. 1 is a graphical representation of the mean sedation vs. time curve for Example 1 (fasted)

Even at steady-state dosages of opioid analgesics, most patients remain in measurable or significant pain. The state-of-the-art approach to controlled release opioid therapy is to provide formulations which exhibit zero order pharmacokinetics and have minimal peak to trough fluctuation in opioid levels with repeated dosing. This zero order release provides very slow opioid absorption, and a generally flat serum concentration curve over time. A flat serum concentration curve is generally considered to be advantageous because it would in effect mimic a steady-state level where efficacy is provided but side effects common to opioid analgesics are minimized. However, by formulating sustained release opioids in this manner, it has been discovered that the patients often experience considerable discomfort at about the time the next oral dose of the opioid is administered.

It has now been surprisingly discovered that quicker and greater analgesic efficacy is achieved by 24 hour oral opioid formulations which do not exhibit a substantially flat serum Concentration curve, but which instead provide a more rapid initial opioid release so that the minimum effective analgesic concentration can be more quickly approached in many patients who have measurable if not significant pain at the time of dosing. Even at steady-state dosages of oral opioid analgesics, most patients have been found to remain in measurable or significant pain and would benefit greatly from treatment with the novel approach to oral opioid treatment disclosed herein. Also surprising and unexpected is the fact that while the methods of the present invention achieve quicker and greater analgesic efficacy, there is not a significantly greater incidence in side effects which would normally be expected as higher peak plasma concentrations occur.

Defining effective analgesic plasma opioid (e.g., morphine) levels is very complex. However, there is generally a "minimally effective analgesic concentration" (MEAC) in plasma for a particular opioid below which no analgesia is provided. While there is an indirect relationship between, e.g., plasma morphine levels and analgesia, higher plasma levels are generally associated with superior pain relief. There is a lag time or hysteresis, between the time of peak plasma opioid levels and the time of peak drug effects. This holds true for the treatment of pain with opioid analgesics in general.

The inventive sustained release once-a-day formulations may be characterized by the fact that they are designed to provide an initially rapid rate of rise in the plasma concentration of said opioid characterized by providing an absorption half-life from about 1 to about 8 hours, when the oral sustained release formulation is administered in the fasted state (i.e., without food). In certain embodiments, the absorption half-life preferably from about 1 to about 6 hours, and more preferably from about 1 to about 3 hours.

The inventive formulations may be further characterized by having a surprisingly fast time to peak drug plasma concentration (i.e., $t_{max}$). The $t_{max}$ of the sustained release formulations of the present invention may be from about 2 to about 10 hours. In certain preferred embodiments, the $T_{max}$ provided by these formulations may be from about 4 to about 9 hours.

The administration of 24-hour opioid oral sustained release formulations in accordance with the present invention reveals a greater degree of intensity of certain pharmacodynamic endpoints during the earlier portions of the plasma concentration curve (e.g., 4–8 hours after oral administration), such as sedation respiratory rate, pupil size, and/or combined scores from a questionnaire of opioid effects reported by the subjects at serial times following each treatment (i.e., administration of the oral dosage form). Other measures of analgesic efficacy such as sum of pain intensity difference (SPID) and total pain relief (TOTPAR) have consistently higher numerical scores via the presently claimed methods, while also generating in many cases fewer adverse events (which in general are predominantly mild or moderate somnolence, nausea and/or dizziness).

Opioid analgesic compounds which may be used in the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. The opioid analgesic may be in the form of the free base, a salt, a complex, etc. In certain preferred embodiments, the opioid analgesic is selected from the group consisting of hydromorphone, oxycodone, dihydrocodeine, codeine, dihydromorphine, morphine, buprenorphine, salts of any of the foregoing, and mixtures of any of the foregoing.

In one preferred embodiment the sustained-release opioid oral dosage form of the present invention includes hydromorphone as the therapeutically active ingredient in an amount from about 4 to about 64 mg hydromorphone hydrochloride. In another preferred embodiment, the opioid analgesic comprises morphine, and the sustained release oral dosage forms of the present invention include form about 5 mg to about 800 mg morphine, by weight. Alternatively, the dosage form may contain molar equivalent amounts of other hydromorphone or morphine salts or of the base. In certain preferred embodiments wherein the opioid is morphine, the maximum plasma concentration is from about 2 ng/ml to about 14 ng/ml, and preferably is from about 3 ng/ml to about 8 ng/ml, based on a 30 mg dose of morphine sulfate. In another preferred embodiment, the opioid analgesic comprises oxycodone, the sustained release oral dosage forms of the present invention include from about 5 mg to about 400 mg oxycodone. In other preferred embodiments, the dosage form contains an appropriate amount of another of the opioid analgesics to provide a substantially equivalent therapeutic effect.

The sustained release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction. Furthermore, the sustained release dosage forms of the present invention preferably releases the opioid analgesic at a rate that is independent of pH, e.g., between pH 1.6 and 7.2. In other words, the dosage forms of the present invention avoid "dose dumping" upon oral administration.

In the present invention, the oral opioid analgesics have been formulated to provide for an increased duration of analgesic action allowing once-daily dosing. Surprisingly, these formulations, at comparable daily dosages of conventional immediate release drug, are associated with a lower incidence in severity of adverse drug reactions and can also be administered at a lower daily dose than conventional oral medication while maintaining pain control.

The retardant material utilized in the sustained release formulations of the invention may be one which is known in the art, including but not limited to acrylic polymers, alkylcelluloses, shellac, zein, hydrogenated vegetable oil, hydrogenated castor oil, and mixtures of any of the foregoing.

In certain preferred embodiments of the present invention, the sustained release opioid dosage forms comprise a plurality of substrates comprising the active ingredient, which substrates are coated with a sustained release coating comprising a retardant material. The coating formulations of the present invention should be capable of producing a strong, continuous film that is smooth and elegant, capable of supporting pigments and other coating additives, non-toxic, inert, and tack-free.

The sustained release preparations of the present invention may be used in conjunction with any multiparticulate system, such as beads, spheroids, microspheres, seeds, pellets, ion-exchange resin beads, and other multiparticulate systems in order to obtain a desired sustained release of the therapeutically active agent. Beads, granules, spheroids, or pellets, etc., prepared in accordance with the present invention can be presented in a capsule or in any other suitable unit dosage form.

When the substrates of the present invention are inert pharmaceutical beads, the inert pharmaceutical beads may be from about 8 mesh to about 50 mesh. In certain preferred embodiments, the beads are, e.g., nu pariel 18/20 beads.

In certain preferred embodiments of the present invention, the sustained release opioid dosage forms comprise a plurality of substrates comprising the active ingredient, which substrates are coated with a sustained release coating. The coating formulations of the present invention should be capable of producing a strong, continuous film that is smooth and elegant, capable of supporting pigments and other coating additives, non-toxic, inert, and tack-free.

In order to obtain a sustained release of the opioid sufficient to provide an analgesic effect for the extended durations set forth in the present invention, the substrate comprising the therapeutically active agent may be coated with a sufficient amount of hydrophobic material to obtain a weight gain level from about 2 to about 30 percent, although the overcoat may be greater depending upon the physical properties of the particular opioid analgesic compound utilized and the desired release rate, among other things.

In order to obtain a sustained release of the opioid sufficient to provide an analgesic effect for the extended durations set forth in the present invention, the substrate comprising the therapeutically active agent may be coated with a sufficient amount of retardant material to obtain a weight gain level from about 2 to about 30 percent, although the overcoat may be greater depending upon the physical properties of the particular opioid analgesic compound utilized and the desired release rate, among other things.

The solvent which is used for the retardant material, which is typically hydrophobic, may be any pharmaceutically acceptable solvent, including water, methanol, ethanol, methylene chloride and mixtures thereof. It is preferable however, that the coatings be based upon aqueous dispersions of the hydrophobic material.

In certain preferred embodiments of the present invention, the hydrophobic polymer comprising the sustained release coating is a pharmaceutically acceptable acrylic polymer, including but not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

In other preferred embodiments, the hydrophobic polymer which may be used for coating the substrates of the present invention is a hydrophobic alkyl cellulosic material such as ethylcellulose. Those skilled in the art will appreciate that other cellulosic polymers, including other alkyl cellulosic polymers, may be substituted for part or all of the ethylcellulose included in the hydrophobic polymer coatings of the present invention.

One commercially available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In embodiments of the present invention where the coating comprises an aqueous dispersion of a hydrophobic polymer, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

The sustained release profile of the formulations of the invention can be altered, for example, by varying the thickness of the hydrophobic coating, changing the particular hydrophysic material used, or altering the relative amounts of, e.g., different acrylic resin lacquers, altering the manner in which the plasticizer is added (e.g., when the sustained release coating is derived from an aqueous dispersion of hydrophobic polymer), by varying the amount of plasticizer relative to hydrophobic polymer, by the inclusion of additional ingredients or excipients, by altering the method of manufacture, etc.

Sustained release spheroids or beads, coated with an opioid may be prepared, e.g. by dissolving the opioid analgesic in water and then spraying the solution onto a substrate, for example, nu pariel 18/20 beads, using a Wurster insert. Optionally, additional ingredients are also added prior to coating the beads in order to assist the opioid binding to the substrates, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic sustained release coating. An example of a suitable barrier agent is one which comprises hydroxypropyl methylcellulose. However, any film-former known in the art may be used. It is preferred that the barrier agent does not affect the dissolution rate of the final product.

The opioid, HPMC protected (optional) beads may then be overcoated with hydrophobic polymer, preferably with an effective amount of plasticizer.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic polymer.

The plasticized aqueous dispersion of hydrophobic polymer may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic polymer to obtain a predetermined sustained-release of said therapeutically active agent when said coated substrate is exposed to aqueous solutions, e.g. gastric fluid, is preferably applied, taking into account the physically characteristics of the therapeutically active agent, the manner of incorporation of the plasticizer, etc. After coating with the hydrophobic polymer, a further overcoat of a film-former, such as Opadry®, is optionally applied to the beads. This overcoat is provided, if at all, in order to substantially reduce agglomeration of the beads.

Next, the coated beads are cured in order to obtain a stabilized release rate of the therapeutically active agent.

When the coating comprises an aqueous dispersion of ethylcellulose, the coated substrate is preferably subjected to curing at a temperature greater than the glass transition temperature of the coating solution (i.e., ethylcellulose) and at a relative humidity from about 60% to about 100%, until the curing endpoint is reached, e.g., about 60° C. and a relative humidity from about 60% to about 100% for a time period from about 48 to about 72 hours, as described in U.S. Pat. No. 5,273,760, hereby incorporated by reference.

In preferred embodiments of the present invention directed to the acrylic coating, a stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours or longer, as described in U.S. Pat. No. 5,286,493, hereby incorporated by reference. The release of the therapeutically active agent from the sustained-release formulation of the present invention can be further influenced, i.e., adjusted to a desired rate, by the addition of one or more release-modifying agents, or by providing one or more passageways through the coating. The ratio of hydrophobic polymer to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic polymers such as hydroxypropylmethylcellulose. The sustained release coatings of the present invention can also include erosion-promoting agents such as starch and gums. The sustained release coatings of the present invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer. In certain preferred embodiments, the release-modifying agent is selected from hydroxypropylmethylcellulose, lactose, metal stearates, and mixtures of any of the foregoing. The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the present invention may utilize a multiparticulate sustained release matrix. Suitable materials for inclusion in a sustained release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

For example, a suitable matrix may be one which comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In certain preferred embodiments, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., at least one hydroxyalkyl cellulose or acrylic resin to at least one aliphatic alcohol/polyalkylene glycol determines, to a considerable extent, the release rate of the opioid from the formulation. A ratio of the at least one hydroxyalkyl cellulose to at least one aliphatic alcohol/polyalkylene glycol of between 1:2 and 1:4 is preferred, with a ratio of between 1:3 and 1:4 being particularly preferred.

At least one polyalkylene glycol may be, for example, polypropylene glycol or, preferably, polyethylene glycol. The number average molecular weight of the at least one polyalkylene glycol is preferred between 1000 and 15000 especially between 1500 and 12000.

Another suitable sustained release matrix would comprise an alkylcellulose (especially ethyl cellulose), a $C_{12}$ to $C_{36}$ aliphatic alcohol and, optionally, a polyalkylene glycol.

In addition to the above ingredients, a sustained release matrix may also contain suitable quantities of other materials, e.g., diluents, lubricants, binders, granulating aids, colorants, flavorants and glidants that are conventional in the pharmaceutical art.

These sustained release matrices may be prepared, for example, by (a) forming granules comprising at least one water soluble hydroxyalkyl cellulose and opioid or an opioid salt, (b) mixing the hydroxyalkyl cellulose containing granules with at least one $C_{12}$–$C_{36}$ aliphatic alcohol, and (c) optionally, compressing and shaping the granules. Preferably, the granules are formed by wet granulating the hydroxyalkyl cellulose/opioid with water. The amount of water added during the wet granulation step may be, e.g., between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred, although hydrous lactose impalpable is preferably utilized for morphine sulfate sustained release formulations prepared by powder-layering techniques. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a water insoluble material such as (a) a wax, either alone or in admixture with a fatty alcohol; or (b) shellac or zein.

The substrates of the present invention may also be prepared via a melt pellitization technique. In such circumstance, the opioid in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

In certain preferred embodiments of the present invention, an effective amount of opioid in immediate release form is included in the 24 hour sustained release unit dose opioid formulation to be administered. The immediate release form of the opioid is included in an amount which is effective to shorten the time to maximum concentration of the opioid in the blood (e.g., plasma). In such embodiments, an effective amount of the opioid in immediate release form may be coated onto the substrates of the present invention. For example, where the extended release opioid from the formulation is due to a controlled release coating, the immediate release layer would be overcoated on top of the controlled release coating. On the other hand, the immediatere lease layer may be coated onto the surface of substrates wherein the opioid is incorporated in a controlled release matrix. Where a plurality of the sustained release substrates comprising an effective unit dose of the opioid (e.g., multiparticulate systems including pellets, spheres, beads and the like) are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims. It has been discovered that by including such an effective amount of immediate release opioid in the unit dose, the experience of relatively higher levels of pain in patients is significantly reduced.

The dosage form may be provided by preparing a dosage form consistent with one of the above described methods or by other means known to those skilled in the pharmaceutical art.

In addition to the above, the sustained release opioid formulations may also be manufactured as tablets. In such instances, the tablet may contain, in addition to the opioid and the retardant material, suitable quantities of other materials, e.g. diluents, lubricants, binders, granulating aids, colorants, flavorants and glidants that are conventional in the pharmaceutical art in amounts up to about 50% by weight of the particulate if desired. Specific examples of pharmaceutically acceptable carriers and excipients that may be used to formulate oral dosage forms are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) Second Edition, published by Marcel Dekker, Inc., incorporated by reference herein. Techniques and compositions for making tablets (compressed and molded), capsules (hard and soft gelatin) and pills are also described in *Remington's Pharmaceutical Sciences*, (Arthur Osol, editor), 1553–1593 (1980), incorporated by reference herein.

In order to titrate a human patient with the inventive sustained release opioid formulations, a plurality of blood samples are taken from the patient over the course of the dosing interval. The samples thus obtained are then tested to determine the plasma level of the opioid analgesic, and any active metabolites thereof. The values thus obtained may then be utilized to determine additional pharmacokinetic parameters. A determination as to whether the patient has obtained an adequate pharmacodynamic response with said dosage form will be made, e.g., reference to predetermined blood levels, comparison of the results subjective pain tests given to the patient, the adverse effect profile of the drug in he patient, or the like. A determination may then be made as to whether an upward or downward adjustment of the dose is necessary.

The administration of the sustained release unit dosage form is continued over the dosing interval of the unit dose to maintain an adequate pharmacodynamic response with the sustained release dosage form. Preferably the adequate pharmacodynamic response will last between about 12 and about 24 hours, most preferably about 24 hours or greater.

The administration of the sustained release unit dosage form is continued over the dosing interval of the unit dose to maintain said adequate pharmacodynamic response with said sustained release dosage form.

If necessary, the above steps are repeated until a determination of adequate pharmacodynamic response is obtained with the sustained release unit dosage form.

According to the above method, a patient may be titrated with a sustained release opioid analgesic dosage form. Subsequent maintenance therapy may be provided with the same sustained release dosage form.

DETAILED DESCRIPTION OF THE PREFERRED EMBODIMENTS

The following examples illustrate various aspects of the present invention. They are not to be construed to limit the claims in any manner whatsoever.

EXAMPLES 1–2

In Example 1, morphine sulfate sustained-release beads with a 5% w/w sustained release coating comprising Eudragit® RS were prepared, including a 10% immediate release morphine sulfate overcoat. In Example 2, morphine sulfate sustained-release beads with an 8% w/w sustained-release coating comprising Eudragit® RS were prepared, including a 10% immediate release morphine sulfate overcoat.

Morphine sulfate beads were first manufactured using a rotor processing technique. The formula of the morphine sulfate beads to which the sustained-release coating was applied is set forth in Table 1 below:

TABLE 1

| Ingredient | Amt/Unit (mg) | Percent (%) |
| --- | --- | --- |
| Morphine Sulfate Powder | 30 mg | 14.3% |
| Lactose Hydrous Impalpable | 42.5 mg | 20.2% |
| PVP | 2.5 mg | 1.2% |
| Sugar Beads 18/20 | 125 mg | 59.4% |
| Purified Water | qs mg | — |
| Opadry Red YS-1-1841 | 10.5 mg | 4.9% |
| Total | 210.5 mg | 100.0% |

A sustained-release coating was then applied to the morphine sulfate beads. The formula for the sustained release coating of Examples 1 and 2 is set forth in Table 2 below:

TABLE 2

| | Example 1 | | Example 2 | |
| --- | --- | --- | --- | --- |
| Ingredient | (mg) | % | (mg) | % |
| Morphine Base Beads | 189.45 mg | 86.7% | 189.5 mg | 83.0% |
| Retardant Coating | | | | |
| Eudragit RS 30D | 9.5 mg | 4.3% | 15.2 mg | 6.7% |
| Triethyl Citrate | 1.9 mg | 0.9% | 3.0 mg | 1.3% |
| Talc | 3.8 mg | 1.7% | 6.1 mg | 2.7% |
| Purified Water | qs | — | qs | — |
| Overcoat | | | | |
| Morphine Sulfate Powder | 3.0 mg | 1.4% | 3.0 mg | 1.3% |
| Opadry Red YS-1-1841 | 10.8 mg | 5.0% | 11.4 mg | 5.0% |
| Purified Water | qs | — | qs | — |
| Total | 218.45 mg | 100.0% | 228.2 mg | 100.0% |

The sustained-release coating was manufactured as follows. The Eudragit RS30D was plasticized with triethyl citrate and talc for approximately 30 minutes. A load of the morphine sulfate beads was charged into a Wurster Insert of a Glatt equipped with a 1.2 mm spray nozzle and the beads were coated to a weight gain of 5% and 8% for Examples 1 and 2, respectively. The final protective Opadry dispersion overcoat was then applied in the Wurster Insert. Upon completion the beads were cured for two days in a dry oven of 45° C. The cured beads were then filled into gelatin capsules at a 30 mg strength.

Dissolution testing was conducted on the gelatin capsules via U.S.P. Apparatus II (Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results of the percent of morphine sulfate dissolved in relation to time for Examples 1 and 2 are set forth in Table 3 below:

TABLE 3

| | Percent Morphine Sulfate Dissolved | |
| --- | --- | --- |
| Time | Example 1 | Example 2 |
| 1 hour | 11.9% | 10.2% |
| 2 hours | 15.4% | 11.3% |
| 4 hours | 28.1% | 12.8% |
| 8 hours | 58.3% | 16.4% |
| 12 hours | 79.2% | 29.6% |
| 18 hours | 92.0% | 58.1% |
| 24 hours | 96.6% | 73.2% |

Clinical Evaluation of Examples 1–2

Ten normal, healthy male subjects were enrolled in a four-way, randomized, single-dose, crossover pharmacokinetic/pharmacodynamic study to characterize the effect of food on the pharmacokinetic/pharmacodynamic profile of Example 1 compared with the same product and with morphine CR 30 mg tablet (MS Contin®), each in the fasted state, using plasma morphine concentration and pharmacodynamic parameters. A comparison of Example 2 with morphine controlled release 30 mg tablet (MS Contin®) was also made. Plasma morphine concentrations were used for calculation of pharmacokinetic parameters including: (a) absorption and elimination rates; (b) area under the curve (AUC); (c) maximum plasma concentration ($C_{max}$); (d) time to maximum plasma concentration $T_{max}$); (e) $T_{1/2}$ (elimination). Pharmacodynamic effect compared with plasma concentrations of morphine was to be described from data obtained from the following pharmacodynamic parameters: mood, sedation, respiratory rate, pupillometry and an adjective questionnaire.

Clinical Laboratory Evaluations

Blood samples were collected for hematology (hemoglobin, hematocrit, red blood cell count, white blood cell count with differential, platelet count) and blood chemistry analyses (calcium, inorganic phosphate, uric acid, total protein, albumin, cholesterol, alkaline phosphatase, lactate dehydrogenase (LDH), total bilirubin, serum glutamic oxaloacetic transaminase (SGOT), serum glutamic pyruvate transaminase (SGPT), fasting blood glucose, blood urea nitrogen (BUN), serum creatinine) pre- and post- (72 hours) study (i.e., 72 hours after Phase 4 dose). A urine sample was collected for urinalysis (specific gravity, glucose, albumin, bile, pH, acetone, microscopic examination) pre- and post- (72 hours) study (i.e., 72 hours after Phase 4 dose). A pre-study urinalysis for illicit drugs was performed during the screening process and immediately pre-dose for each administration of the study drug (Day 1 of Phases 1 through 4).

Plasma morphine concentrations were determined from blood samples which were drawn just prior to dosing (0 hour) and thereafter at 0.5, 1, 2, 2.5, 3, 3.5, 4, 5, 6, 8, 10, 12, 18, 24, 36, 48 and 72 hours following each dose. Blood samples, each approximately 10 ml, were drawn into tubes containing ethylenediaminetetraacetic acid (EDTA) solution, an anticoagulant. Following centrifugation, the plasma was pipetted into two 5-ml polypropylene, labeled tubes and frozen at −20° C. One set of samples was shipped to the designated analytical laboratory in sufficient dry ice to keep them frozen for 2 days, and the second set was retained frozen at the study site as a back-up.

Pharmacodynamic Measurements

Measurements of the following pharmacodynamic parameters were made just prior to blood sampling at baseline (within 30 minutes prior to dosing) and thereafter at 0.5, 1, 2, 2.5, 3, 3.5, 4, 5, 6, 8, 10, 12, 18, 24, 36, 48 and 72 hours following each dose.

Mood (measured by a visual analog scale (VAS) on a subject diary sheet)—10 minutes prior to blood sampling. The VAS was anchored on one end as Worst Mood and the other end as Best hood.

Sedation (measured by VAS on a subject diary sheet)—10 minutes prior to blood sampling. The VAS was anchored on one end as Asleep and the other end as Awake.

Respiratory rate (breaths per minute)—within 5 minutes of blood sampling. (Data were recorded on a subject diary sheet.)

Pupil size—measured by pupillometry—within 5 minutes of blood sampling. Only the left eye was measured at all time periods. (Data were recorded on a subject diary sheet.)

Figure 2:
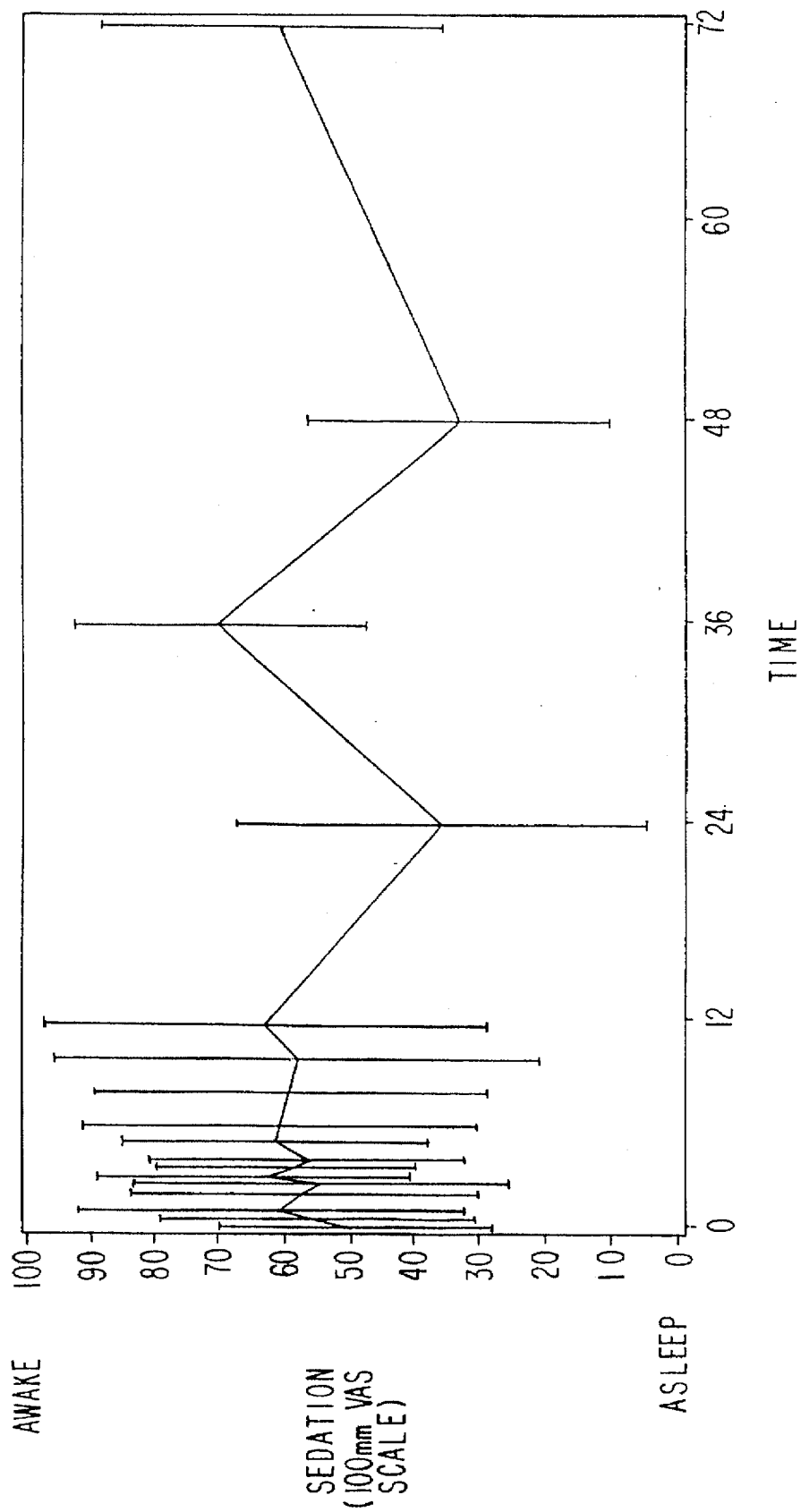
FIG. 2 is a graphical representation of the mean sedation vs. time curve for Example 2 (fasted)
Figure 3:
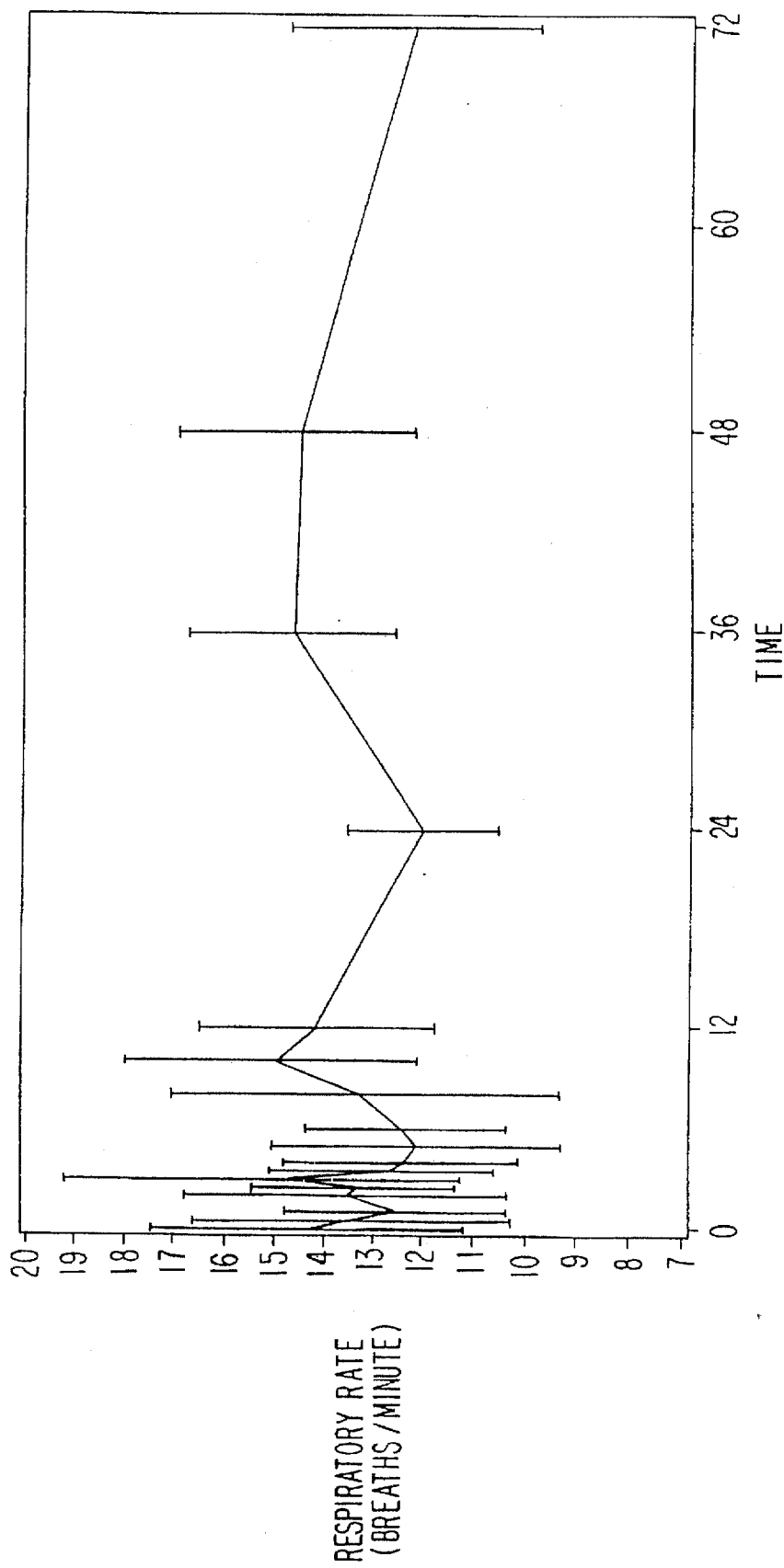
FIG. 3 is a graphical representation of the mean respiratory rate vs. time curve for Example 1 (fasted)
Figure 4:
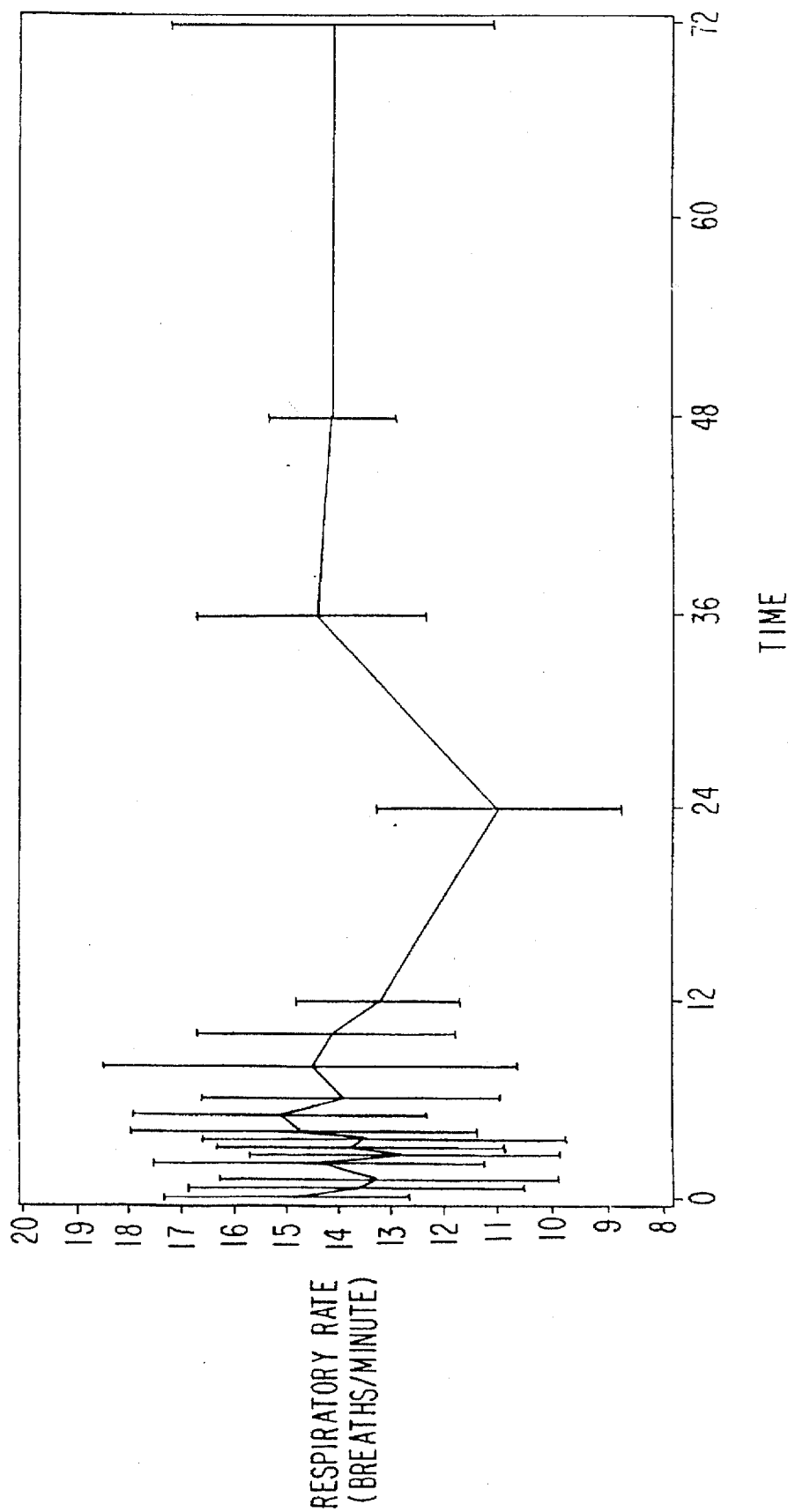
FIG. 4 is a graphical representation of the mean respiratory rate vs. time curve for Example 2 (fasted)

FIG. 1 is a graphical representation of the mean sedation vs. time curve for Example 1 (fasted). FIG. 2 is a graphical representation of the mean sedation vs. time curve for Example 2 (fasted). FIG. 3 is a graphical representation of the mean respiratory rate vs. time curve for Example 1 (fasted). FIG. 4 is a graphical representation of the mean respiratory rate vs. time curve for Example 2 (fasted).

Plasma morphine concentrations were determined by a high-performance liquid chromatographic procedure. Arithmetic mean Cmax, Tmax, AUC, half-lives calculated from individual plasma morphine concentration-versus-time, and oral bioavailability data were as set forth in Tables 4 and 5 below:

TABLE 4

| Pharmacokinetic Parameter | MS Contin® (Fast) | Ex. 2 (Fast) | Ex. 1 (Fast) | Ex. 1 (Fed) |
|---|---|---|---|---|
| $C_{max}$ (ng/ml) | 13.05 | 3.95* | 5.42* | 5.87* |
| $T_{max}$ (hours) | 2.45 | 15.05* | 5.85 | 6.90 |
| AUC (0,72) (hr-ng/ml) | 101.11 | 136.10* | 109.37 | 111.33 |
| AUC (0,00) (hr-ng/ml) | 101.31 | 155.44* | 117.77 | 114.45 |
| $T_{1/2}$ (elim; hrs) | 2.81 | 89.68* | 19.02 | 10.34 |
| $T_{1/2}$ (abs; hrs) | 1.20 | 3.96 | 2.51 | 3.48 |

TABLE 5

(A = MS Contin; B = Example 2 fasted; C = Example 1 Fed; and D = Example 1 fasted)

| Pharmacokinetic Parameter | $F_0$ (%) 90% C.I. (B vs. A) | $F_0$ (%) 90% C.I. (C vs. A) | $F_0$ (%) 90% C.I. (D vs. A) | $F_0$ (%) 90% C.I. (D vs. C) |
|---|---|---|---|---|
| $C_{max}$ (ng/ml) | 32.24 (15.7–48.7) | 39.88 (23.3–56.5) | 42.50 (26.0–59.0) | 106.57 (65.2–148.0) |
| Tmax (hours) | 608.27 (435.6–780.9) | 232.33 (58.8–405.8) | 290.48 (117.9–463.11) | 125.03 (50.7–199.3) |
| AUC (0,72) (hr-ng/ml) | 134.53 (111.1–158.0) | 105.02 (81.5–128.6) | 106.04 (82.6–129.5) | 100.97 (78.6–123.3) |
| AUC (0,00) (hr-ng/ml) | 151.04 (112.6–189.4) | 112.91 (81.8–144.0) | 108.09 (77.1–139.0) | 95.73 (68.3–123.1) |
| $T_{1/2}$ (elim; hrs) | 3076.7 (2256.7–3896.7) | 689.41 (24.9–1353.9) | 374.01 (−286.8–1034.9) | 54.25 (−41.6–150.1) |
| $T_{1/2}$ (abs; hrs) | 281.21 (−123.1–685.5) | 167.18 (−11.7–346.0) | 239.86 (62.4–417.3) | 143.48 (37.2–249.8) |

TABLE 5-continued (A = MS Contin; B = Example 2 fasted; C = Example 1 Fed; and D = Example 1 fasted)

| Pharmacokinetic Parameter | $F_0$ (%) 90% C.I. (B vs. A) | $F_0$ (%) 90% C.I. (C vs. A) | $F_0$ (%) 90% C.I. (D vs. A) | $F_0$ (%) 90% C.I. (D vs. C) |
|---|---|---|---|---|

*Statistically significant (p <.0500) when compared to MS Contin® (based on untransformed data)
$F_0$ (%) = Oral bioavailability (Test least squares mean/Reference least squares mean)

Table 6 provides the mean (±S.D.) plasma morphine concentrations (ng/ml) following dosing with MS Contin® and Examples 1 and 2.

TABLE 6

Mean (± S.D.) Plasma Morphine Concentrations (ng/ml) Following Dosing With MS Contin® And Each Formulation Of Morphine Beads

| Time (hours) | MS Contin® 30 mg (Fast) | Ex. 2 (Fast) | Ex. 1 (Fast) | Ex. 1 (Fed) |
|---|---|---|---|---|
| 0.00 | 0.00 ± 0.00 | 0.00 ± 0.00 | 0.00 ± 0.00 | 0.00 ± 0.00 |
| 0.50 | 3.04 ± 2.07 | 2.22 ± 1.09 | 1.82 ± 1.35 | 0.51 ± 0.79 |
| 1.00 | 6.78 ± 4.19 | 1.89 ± 0.54 | 2.09 ± 1.07 | 1.46 ± 0.95 |
| 2.00 | 11.43 ± 5.70 | 1.60 ± 0.69 | 2.33 ± 0.98 | 2.46 ± 0.91 |
| 2.50 | 10.30 ± 6.46 | 1.78 ± 1.16 | 2.22 ± 0.88 | 2.51 ± 0.88 |
| 3.00 | 9.40 ± 5.41 | 1.54 ± 0.97 | 2.61 ± 1.12 | 3.47 ± 1.77 |
| 3.50 | 8.09 ± 4.48 | 1.34 ± 0.98 | 2.82 ± 1.39 | 3.03 ± 1.26 |
| 4.00 | 7.11 ± 3.78 | 1.06 ± 0.49 | 3.60 ± 2.50 | 3.41 ± 1.82 |
| 5.00 | 7.25 ± 4.71 | 1.54 ± 1.21 | 4.09 ± 2.24 | 3.80 ± 1.29 |
| 6.00 | 5.27 ± 3.31 | 1.20 ± 0.77 | 4.11 ± 1.74 | 4.23 ± 1.68 |
| 8.00 | 3.19 ± 1.99 | 1.58 ± 1.00 | 3.80 ± 1.46 | 4.46 ± 1.51 |
| 10.0 | 1.87 ± 1.00 | 2.62 ± 1.05 | 3.57 ± 1.44 | 4.16 ± 1.37 |
| 12.0 | 1.70 ± 0.76 | 3.10 ± 1.64 | 2.83 ± 0.64 | 4.33 ± 2.20 |
| 18.0 | 1.23 ± 0.67 | 3.04 ± 1.11 | 2.40 ± 1.13 | 1.85 ± 1.12 |
| 24.0 | 1.38 ± 0.96 | 2.54 ± 0.55 | 1.82 ± 1.01 | 1.71 ± 0.73 |
| 36.0 | 0.85 ± 0.64 | 2.58 ± 1.04 | 1.35 ± 0.70 | 1.19 ± 0.40 |
| 48.0 | 0.22 ± 0.47 | 1.48 ± 0.48 | 0.69 ± 1.08 | 0.73 ± 0.56 |
| 72.0 | 0.05 ± 0.16 | 0.54 ± 0.66 | 0.16 ± 0.33 | 0.22 ± 0.46 |

Table 7 provides the mean (±S.D.) pharmacokinetic parameters following dosing with MS Contin® And Examples 1-2.

TABLE 7

Mean (± S.D.) Pharmacokinetic Parameters Following Dosing With MS Contin® And Each Formulation Of Morphine Beads

| Parameter | MS Contin® 30 mg (Fast) | Ex. 2 (Fast) | Ex. 1 (Fast) | Ex. 1 (Fed) |
|---|---|---|---|---|
| $C_{max}$ (ng/ml) | 13.05 ± 5.22 | 3.95 ± 1.55 | 5.42 ± 2.26 | 5.87 ± 2.07 |
| Tmax (hrs) | 2.45 ± 0.86 | 15.05 ± 9.51 | 5.85 ± 1.92 | 6.90 ± 3.18 |
| AUC (0,72) (hr-ng/ml) | 101.11 ± 41.913 | 136.10 ± 34.58 | 109.37 ± 43.06 | 111.33 ± 36.21 |

In comparing Example 1 (fast) to MS Contin® (fast), there was a statistically significant difference in $C_{max}$. There were no statistically significant differences between the two treatments in $T_{max}$, AUC (0,72), AUC (O, oo) and $T_{1/2}$ (elim) or $T_{1/2}$ (abs). The 90% confidence intervals for all pharmacokinetic parameters were outside the 80–120% limits.

In comparing Example 1 (fed) to MS Contin® (fast), there was a statistically significant difference in $C_{max}$. There were no statistically significant differences between the two treatments in $T_{max}$, AUC (0,72), AUC (O, oo) and $T_{1/2}$ (elim) or T$_{1/2}$ (abs). The 90% confidence intervals for all pharmacokinetic parameters were outside the 80–120% limits.

In comparing Example 1 under fed and fasting conditions, there were no statistically significant differences in C$_{max}$, T$_{max}$, AUC (0,72), AUC (O, oo) and T$_{1/2}$ (elim) or T$_{1/2}$ (abs). The 90% confidence intervals for all pharmacokinetic parameters were outside the 80–120% limits.

The effect of food on the absorption of Example 1 is characterized by a greater C$_{max}$ and extended T$_{max}$ and T$_{1/2}$ (abs) values. The extent of absorption (based on AUCs), however, is less than 3% different under fed and fasted conditions.

In comparing Example 2 (fast) to MS Contin® (fast), there were statistically significant differences in C$_{max}$, T$_{max}$, AUC (0,72), AUC (O, oo) and T$_{1/2}$ (elim). There was no statistically significant difference between the two treatments in T½ (abs). The 90% confidence intervals for all pharmacokinetic parameters were outside the 80–120% limits.

Based on the 90% confidence interval analysis, neither Example 1 under fasted or fed conditions nor Example 2 beads are equivalent to MS Contin® tablets. However, while neither of the experimental controlled-release morphine formulations are bioequivalent to MS Contin® tablets, both provide a relatively lower C$_{max}$ and extended T$_{max}$ and apparent T$_{1/2}$ (elim) values.

Linear regression of each pharmacodynamic parameter on the log-transformed concentrations for each subject and treatment resulted in 48 of 240 regressions (48/240; 20%) having an R$^2$ value of 20% or higher, of which 8 (8/240; 3%) had a value of 50% or higher. When analyzed by treatment only, all R$^2$ values were lower than 10%. These values indicate no significant linear relationship between the pharmacodynamic measurements and the log concentrations.

Figure 5:
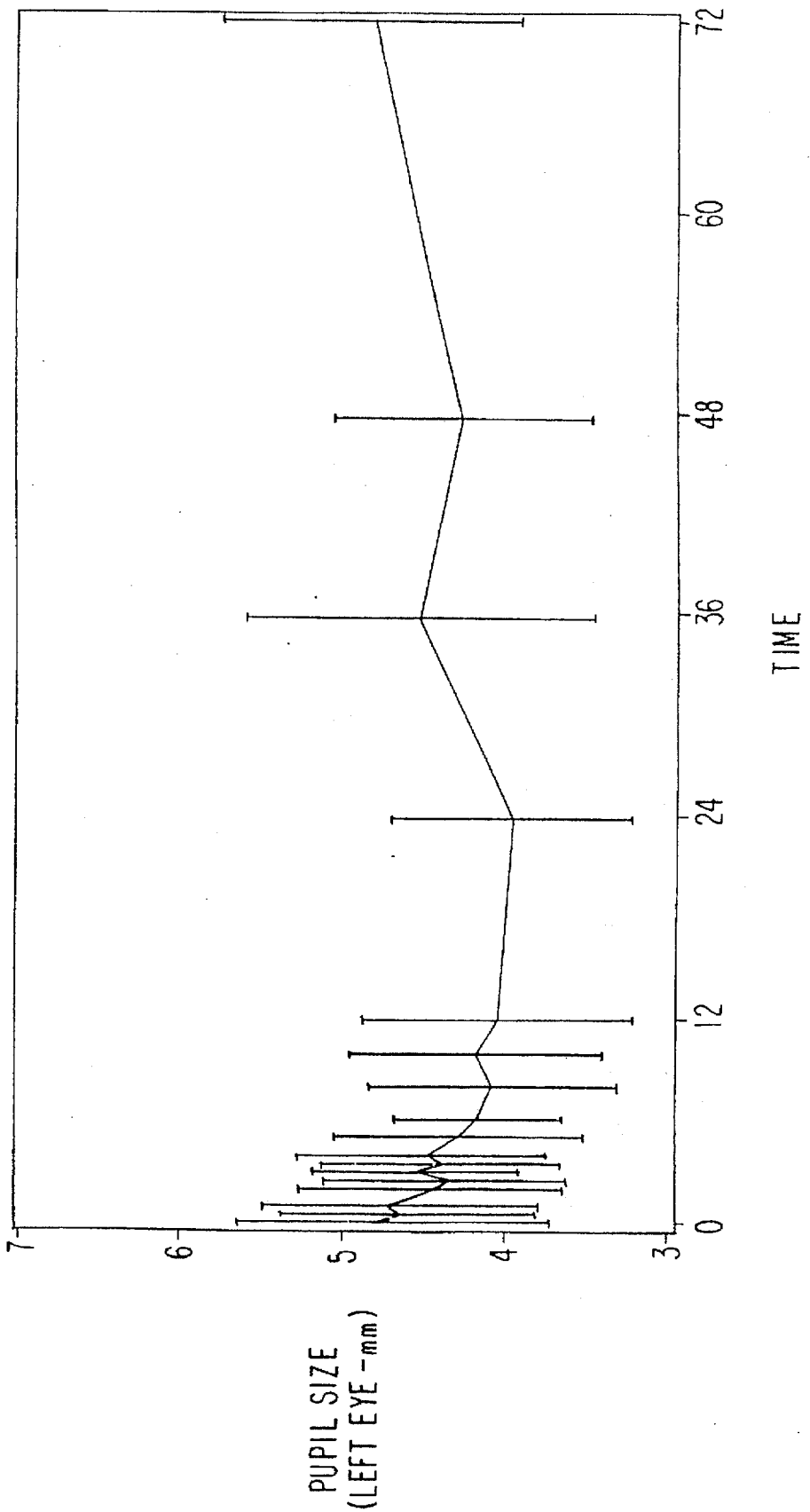
FIG. 5 is a graphical representation of the mean pupil size v. time curve for Example 1 (fasted)
Figure 6:
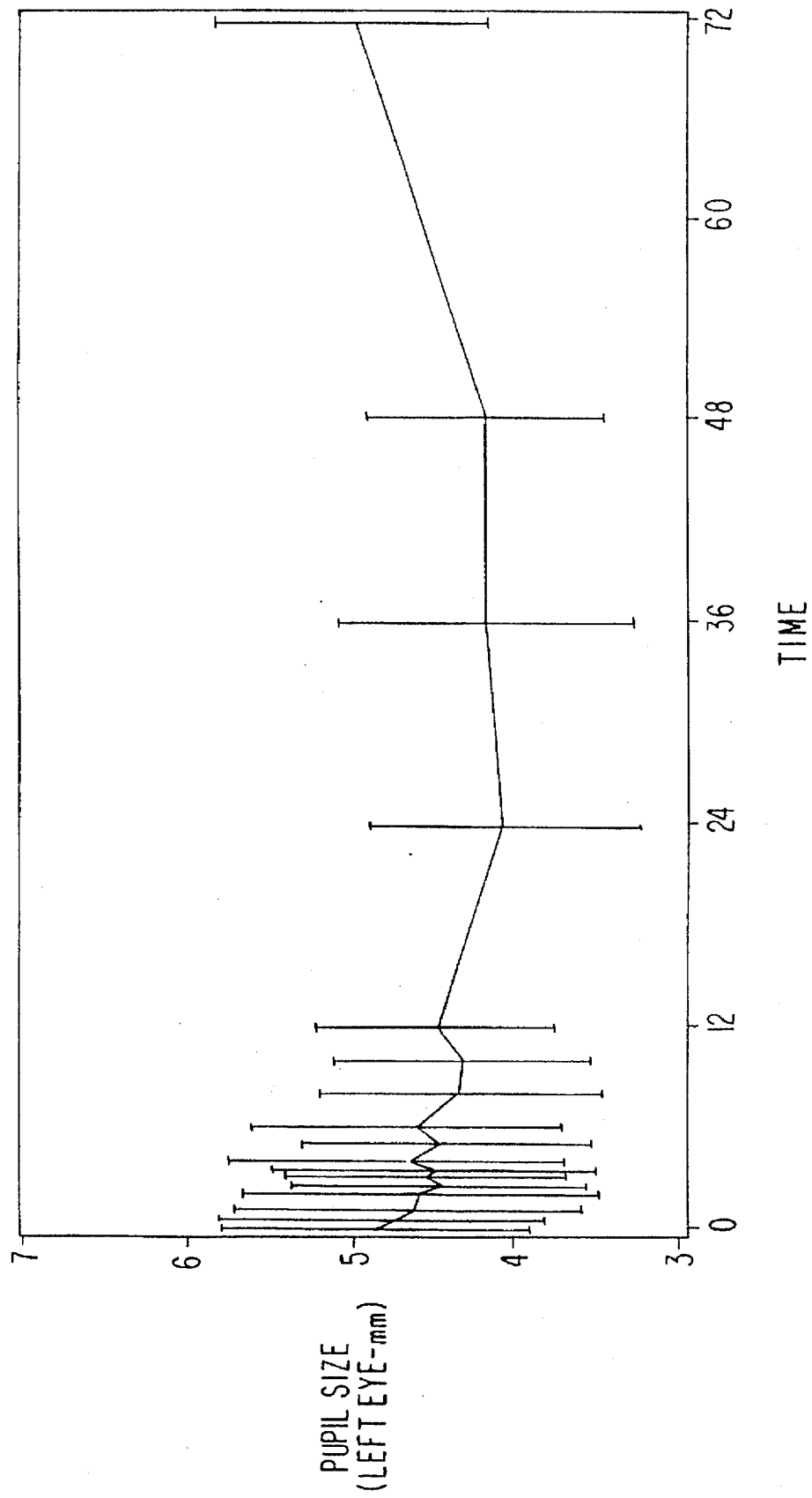
FIG. 6 is a graphical representation of the mean pupil size vs. time curve for Example 2 (fasted)

Examination of the mean hysteresis curves revealed a possible relationship between pupil size and morphine concentration. For MS Contin® and Example 1, pupil size tended to decrease with an increase in morphine concentration, then increase as morphine concentration decreased. FIG. 5 is a graphical representation of the mean pupil size v. time curve for Example 1 (fasted). FIG. 6 is a graphical representation of the mean pupil size vs. time curve for Example 2 (fasted). No relationship was observed between morphine concentrations and any of the other parameters.

Two subjects (20%) reported six adverse experiences while receiving MS Contin®. Three subjects (30%) reported six adverse experiences while receiving controlled-release morphine beads (Example 1; fasted). One subject in each of the following treatment groups reported a single adverse experience: Example 1 (fed) and Example 2 (fasted). No clinically significant changes in physical examination or EKG results, clinical laboratory values or vital sign measurements occurred during the study.

Modified Specific Drug Effect Questionnaire

The questionnaire was a modification of the 22-item questionnaire used by Jasinski, D. R. (1977) Assessment of the Abuse Potential of Morphine-Like Drugs (Methods Used in Man). In *Drug Addiction* (Martin, W. R., ed.) pp. 197–258. Springer-Verlag, New York; and Preston, K. L., Jasinski, D. R., and Testa, M. (1991) Abuse Potential and Pharmacological Comparison of Tramadol and Morphine. *Drug and Alcohol Dependence* 27:7–17. The questionnaire consisted of 10 items to be rated by the subject and observer. The items were related to signs of opiate-agonist drugs and were as follows:

Subject's Questions
1. Do you feel any effects of the drugs?
2. Is your skin itchy?
3. Are you relaxed?
4. Are you sleepy?
5. Are you drunk?
6. Are you nervous?
7. Are you full of energy?
8. Do you need to talk?
9. Are you sick to your stomach?
10. Are you dizzy?

The subject rated each of these questions by placing a vertical mark along a 100-mm VAS anchored at one end by "not at all" and at the other end by "an awful lot".

Observer's Questions
1. Is the subject showing any drug effect?
2. Is the subject scratching?
3. Is the subject relaxed?
4. Is the subject drunk?
5. Is the subject nervous?
6. Is the subject talking?
7. Is the subject vomiting?
8. Is the subject confused?
9. Is the subject restless?
10. Is the subject perspiring?

Figure 7:
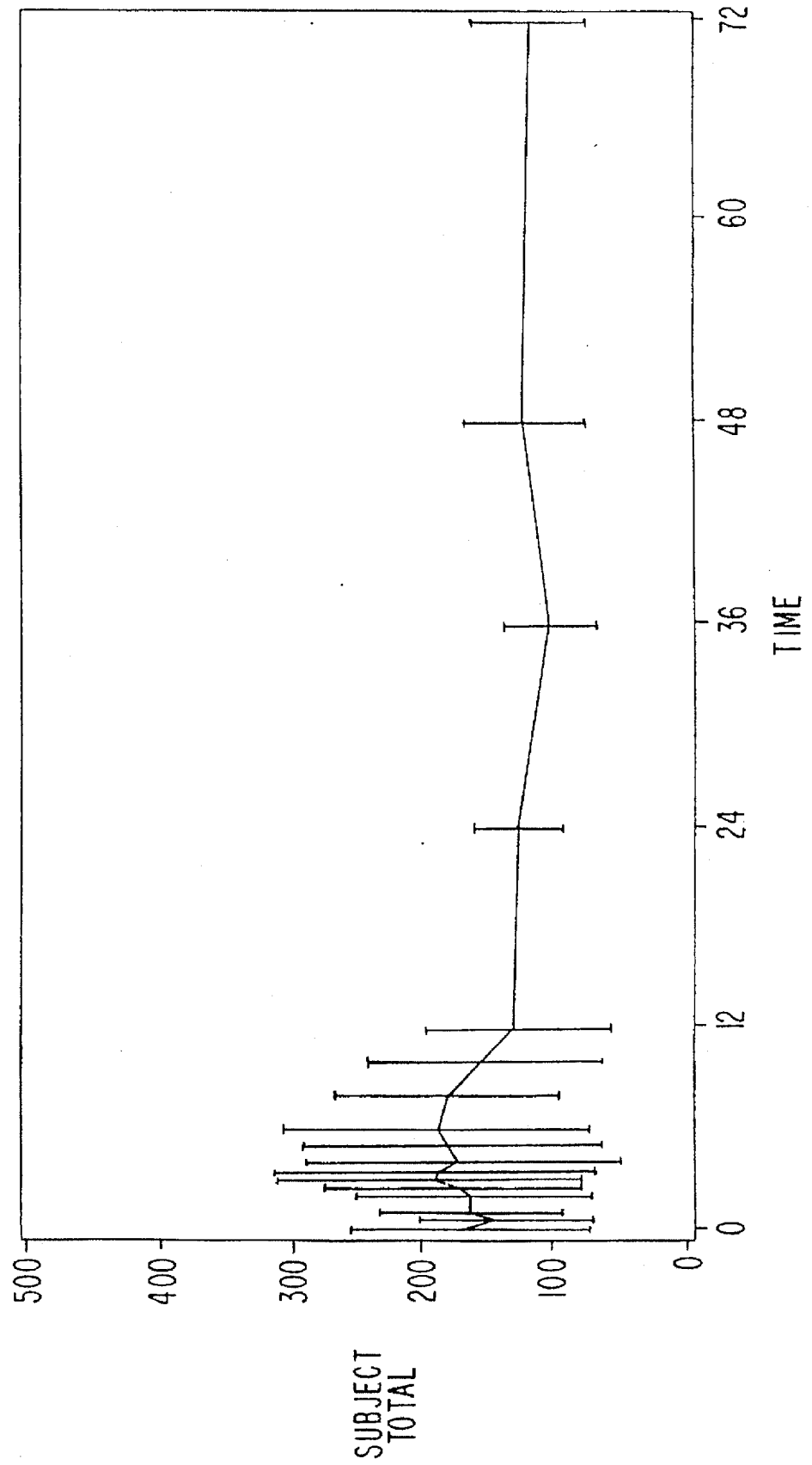
FIG. 7 is a graphical representation of the means subject questionnaire vs. time curve for Example 1 (fasted)
Figure 8:
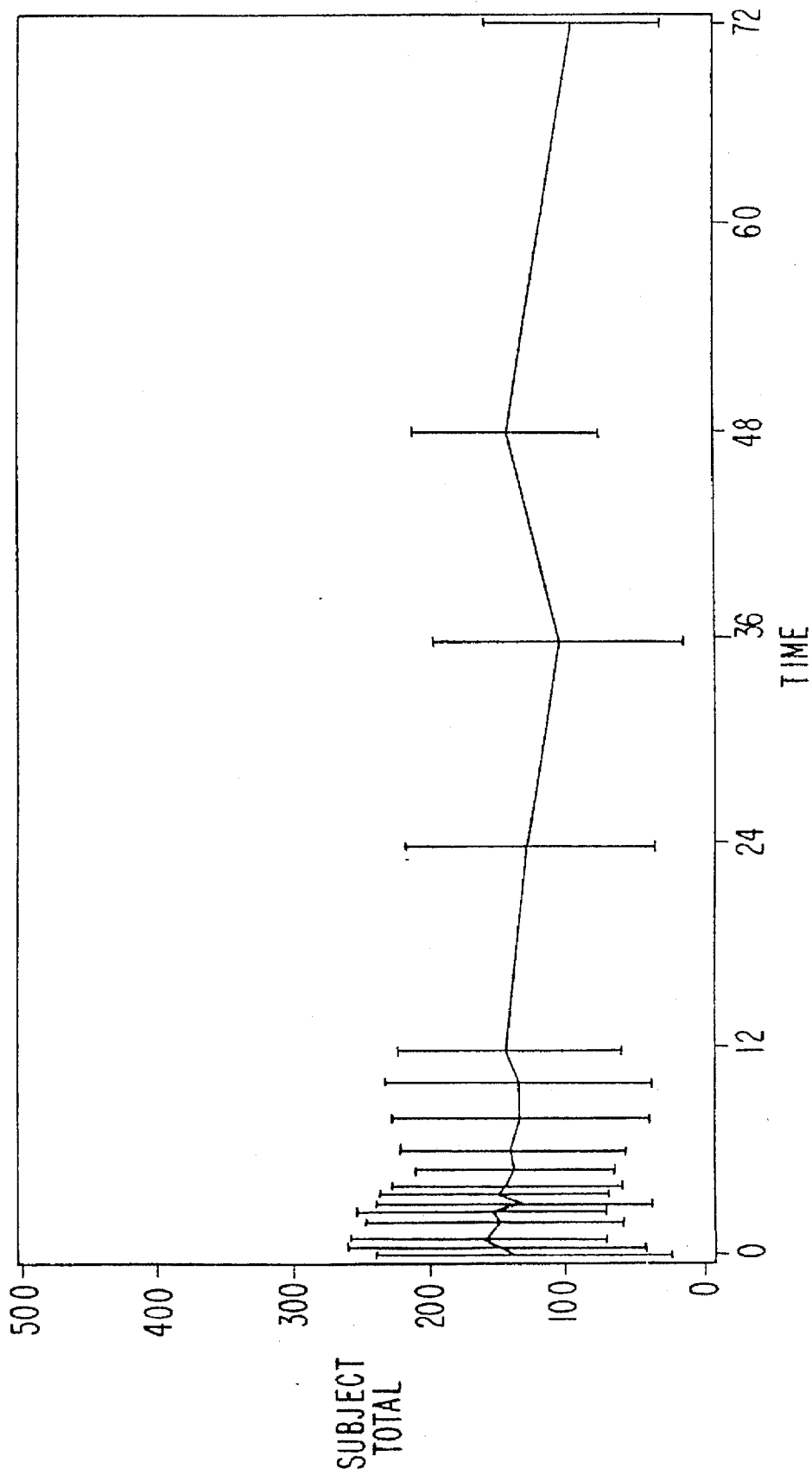
FIG. 8 is a graphical representation of the means subject questionnaire vs. time curve for Example 2 (fasted)

The observer rated each of these questions by placing a vertical mark along a 100-mm VAS anchored at one end by "not at all" and at the other end by "extremely". FIG. 7 is a graphical representation of the means subject questionnaire vs. time curve for Example 1 (fasted). FIG. 8 is a graphical representation of the means subject questionnaire vs. time curve for Example 2 (fasted).

Adverse Experiences

Adverse experiences, whether spontaneously reported or elicited upon direct questioning, were recorded and evaluated promptly by the principal investigator to determine the severity, duration and initiation of corrective measures, if warranted. Subjects were to be followed until they returned to baseline status.

Analytical

Plasma morphine analyses were conducted using high performance liquid chromatography (HPLC). The limit of quantification was 0.5 ng/mL.

Statistical and Pharmacometric Methods

Parameters

The serial plasma morphine values, collected from each subject and treatment, were corrected for the zero-hour value by subtraction of the zero-hour value from all subsequent values in that series.

Any serial dataset in which the zero-hour value exceeded the minimum assay sensitivity was, as noted above, deemed inadmissible for data analysis. The following parameters were estimated for each subject and treatment, using the baseline-corrected plasma levels:

C$_{max}$ (ng/ml)—largest observed plasma morphine value

T$_{max}$ (hours)—time of occurrence of C$_{max}$, relative to time of dosing

T$_{1/2}$ (elim; hours)—apparent half-life of plasma morphine elimination calculated according to:

$$T_{1/2}(elim)=0.693/K_e$$

where K$_e$ is the terminal first-order apparent elimination rate constant calculated by PROC NLIN in SAS Release 6.07 (SAS Institute, Cary, N.C.).

T$_{1/2}$ (abs; hrs)—apparent half-life of absorption calculated according to:

$T_{1/2}(abs)=0.693/K_a$

Figure 9:
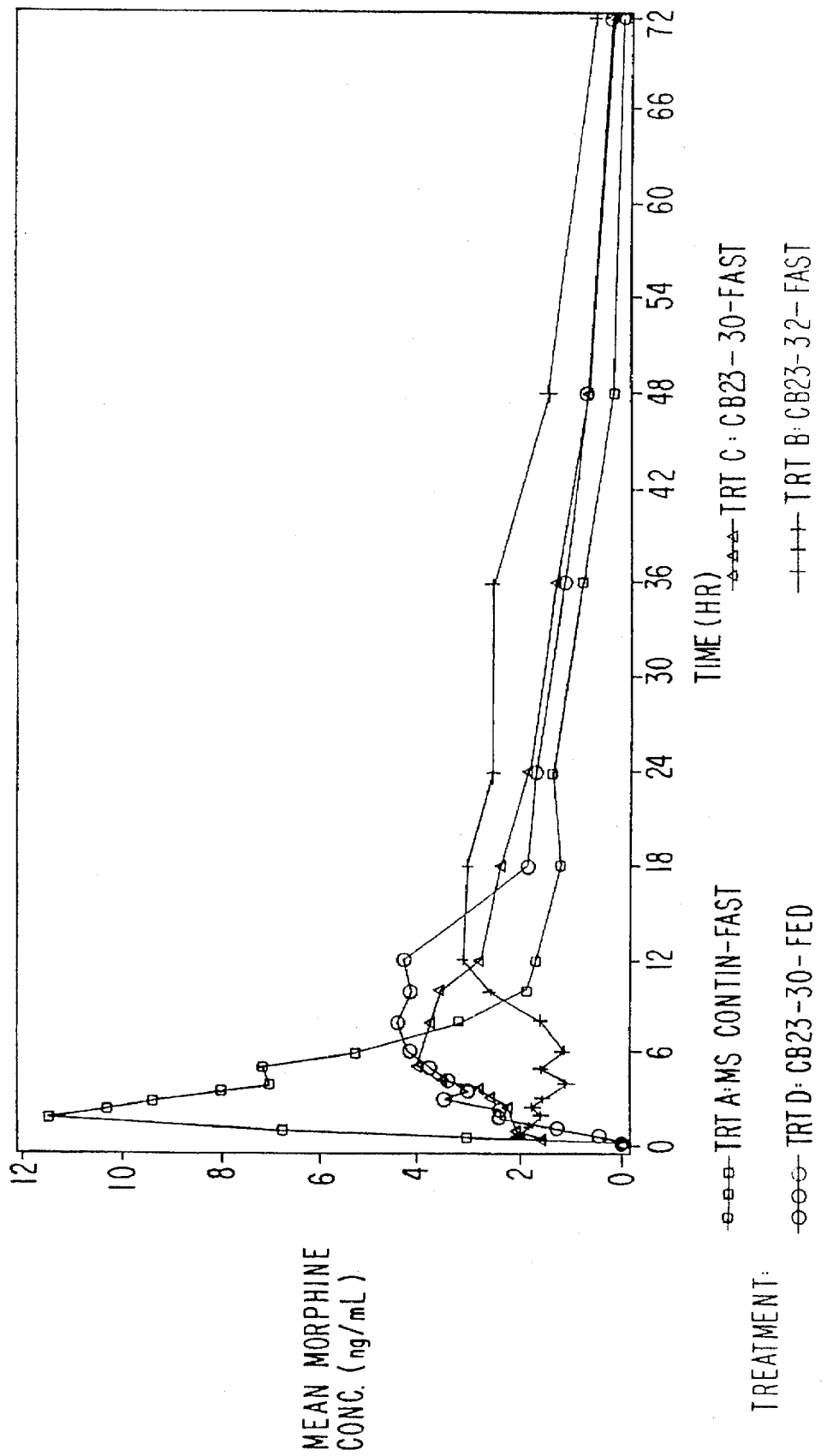
FIG. 9 is a graphical representation of the mean plasma morphine concentration-time profile obtained with the Comparative Example (MS Contin 30 mg) (fasted) as compared to the capsules of Example 1 (fed and fasted) and Example 2 (fasted)

FIG. 9 is a graphical representation of the mean plasma morphine concentration-time profile obtained with the Comparative Example (MS Contin 30 mg) (fasted) as compared to the capsules of Example 1 (fed and fasted) and Example 2 (fasted).

From the results set forth above, it can be seen that the formulation of Example 1 attains a higher and earlier Cmax but a slightly lower extent of morphine absorption than the formulation of Example 2. Visual examination of the time-action data in respect to sedation, respiratory rate, pupil size, and combined scores from a questionnaire of opioid effects reported by the subjects at serial times following each treatment reveals greater degree of intensity of each pharmacodynamic endpoint during the earlier (e.g., 4–8 hours) portion of the time-action curves.

EXAMPLE 3

Beads with a higher loading of morphine sulfate were produced with the use of the powder layering technique in the Glatt Rotor Processor. The formulation of the high load beads is set forth in Table 8 below:

TABLE 8

| Ingredient | High Load Bead mg/unit | Percent (%) |
|---|---|---|
| Morphine Sulfate Powder | 30.0 mg | 63.3% |
| Lactose | 6.0 mg | 12.7% |
| Povidone C-30 | 1.25 mg | 2.6% |
| Sugar Beads | 7.75 mg | 16.4% |
| Opadry | 2.37 mg | 5.0% |
| Purified Water | qs | — |
| Total | 47.37 mg | 100.0% |

The sustained-release coating comprised an acrylic polymer (i.e., Eudragit® RL). A HPMC protective coat was also included between the Eudragit layer and the morphine immediate release layer to further enhance stability. The formula of the sustained release coating of Example 1 is set forth in Table 9 below:

TABLE 9

| Ingredient | Amt/Unit (mg) | Percent (%) |
|---|---|---|
| Morphine (high load) base beads | 42.63 mg | 78.8% |
| Retardant Coating | | |
| Eudragit RS 30D | 2.1 mg | 3.9% |
| Eudragit RL 30D | 0.05 mg | 0.1% |
| Triethyl Citrate | 0.45 mg | 0.8% |
| Talc | 0.85 mg | 1.6% |
| Overcoatings | | |
| Opadry Blue YS-1-10542A | 2.45 mg | 4.5% |
| Purified Water | qs | — |
| Morphine Sulfate Powder | 3.0 mg | 5.5% |
| Opadry Blue YS-1-10542A | 2.55 mg | 4.8% |
| Purified Water | qs | — |
| Total | 54.08 mg | 100.0% |

The sustained release and the immediate release coatings were applied as follows. The Eudragit RL 30D was plasticized with triethyl citrate and talc for approximately 30 minutes. A load of the morphine sulfate beads was charged into a Wurster Insert of a Glatt equipped with a 1.2 mm spray nozzle and the beads are coated to a weight gain of 5%. The final protective Opadry dispersion overcoat was then applied in the Wurster Insert. Upon completion the beads were cured for two days in a dry oven of 45° C. The cured beads were then filled into gelatin capsules at a 30 mg strength. The cured beads were then filled into gelatin capsules at a strength of 30 mg.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results of dissolution testing is set forth in Table 10 below:

TABLE 10

| Time | Percent Morphine Sulfate Dissolved |
|---|---|
| 1 hour | 11.7% |
| 2 hours | 12.1% |
| 4 hours | 22.0% |
| 8 hours | 45.3% |
| 12 hours | 63.7% |
| 18 hours | 81.8% |
| 24 hours | 92.5% |

Clinical Evaluation of Example 3

Thirteen normal, healthy male subjects were enrolled in this five-way crossover, randomized, open-label study assessing the effect of food on the pharmacokinetics and pharmacodynamics of single 30-mg doses (capsules) of Example 3. The pharmacokinetic and pharmacodynamic results of the extended-release formulations in these fed and fasted subjects were also compared with those of MS Contin® 30 mg tablets in fasted subjects. Plasma morphine level was used to calculate pharmacokinetic parameters including: (a) apparent absorption and elimination rates; (b) area-under-the-curve (AUC); (c) maximum plasma concentration ($C_{max}$); (d) time to maximum plasma concentration ($T_{max}$); (e) $T_{1/2}$ (abs), and (f) $T_{1/2}$ (elim). Pharmacodynamic effects were assessed based on evaluations of mood, sedation, respiratory rate, pupillometry, and subject's adjective questionnaire.

Plasma morphine concentrations were determined by a high-performance liquid chromatographic procedure. All subjects completed the study and were included in the biopharmaceutical analysis. Arithmetic mean $C_{max}$, $T_{max}$, AUC, half-lives calculated from individual plasma morphine concentration-versus-time, and oral bioavailability data are set forth in Tables 11 and 12 below:

TABLE 11

| Pharmacokinetic Parameter | Ex. 3 (Fed) | Ex. 3 (Fast) | MS Contin ® (Fasted) |
|---|---|---|---|
| $C_{max}$ (ng/ml) | 5.45 | 4.03 | 11.65 |
| $T_{max}$ (hours) | 8.04 | 12.92 | 2.77 |
| AUC (0,72) (hr-ng/ml) | 118.12 | 140.79 | 114.05 |
| AUC (0,00) (hr-ng/ml) | 137.67 | 166.19 | 114.05 |
| $T_{1/2}$ (elim; hrs) | 21.19 | 54.51 | 1.26 |
| $T_{1/2}$ (abs; hrs) | 3.12 | 2.44 | 3.34 |

TABLET 12

| Pharmaco-kinetic Parameter | $F_0$ (%) 90% C.I. (Ex 3: Fed vs. Fast) | Ex. 3 vs. MS Contin® (Both Fasted) |
|---|---|---|
| $C_{max}$ (ng/ml) | 164.36 (113.1–215.6) | 29.54 (14.3–44.7) |
| $T_{max}$ (hours) | 53.49 (13.3–93.7) | 514.28 (306.8–721.7) |
| AUC (0,72) (hr-ng/ml) | 89.93 (64.8–115.1) | 119.35 (89.2–149.5) |
| AUC (0,00) (hr-ng/ml) | 86.56 (62.5–110.6) | 143.48 (108.6–178.1) |
| $T_{1/2}$ (elim; hrs) | 34.53 (7.4–61.7) | 1609.0 (1170–2048) |
| $T_{1/2}$ (abs; hrs) | 135.27 (83.5–187.0) | 191.45 (92.0–290.9) |

$F_0$ (%) = oral bioavailability (Test mean/Reference mean)

Table 13 provides the mean (±S.D.) plasma morphine concentrations (ng/ml) following dosing with MS Contin® and Example 3.

TABLE 13

Mean Plasma Morphine Concentrations ± Standard Deviation Following Administration

| Time (hours) | Ex. 3 30 mg Fed | Ex. 3 30 mg Fasted | MS Contin® 30 mg Fasted |
|---|---|---|---|
| 0.00 | 0.00 ± 0.00 | 0.00 ± 0.00 | 0.00 ± 0.00 |
| 0.50 | 0.201 ± 0.447 | 2.00 ± 1.48 | 3.42 ± 1.82 |
| 1.00 | 0.331 ± 0.479 | 2.27 ± 0.799 | 6.09 ± 2.03 |
| 2.00 | 1.65 ± 1.53 | 2.19 ± 0.936 | 8.82 ± 2.61 |
| 2.50 | 3.06 ± 1.04 | 2.20 ± 0.798 | 9.12 ± 2.97 |
| 3.00 | 3.53 ± 1.82 | 2.24 ± 1.05 | 9.91 ± 5.32 |
| 3.50 | 3.06 ± 1.16 | 2.87 ± 1.94 | 8.83 ± 3.58 |
| 4.00 | 3.23 ± 1.04 | 2.33 ± 1.13 | 8.12 ± 3.26 |
| 5.00 | 4.01 ± 1.50 | 2.91 ± 0.933 | 7.79 ± 3.47 |
| 6.00 | 4.00 ± 2.09 | 2.96 ± 1.24 | 6.07 ± 3.69 |
| 8.00 | 4.03 ± 1.90 | 2.58 ± 1.24 | 4.68 ± 3.88 |
| 10.0 | 3.95 ± 1.89 | 1.95 ± 0.965 | 2.61 ± 1.43 |
| 12.0 | 3.20 ± 1.47 | 2.18 ± 0.983 | 1.58 ± 0.815 |
| 18.0 | 2.06 ± 1.02 | 2.75 ± 1.53 | 1.46 ± 0.745 |
| 24.0 | 2.10 ± 0.963 | 2.72 ± 0.971 | 1.34 ± 0.890 |
| 36.0 | 1.66 ± 1.05 | 2.65 ± 1.18 | 1.08 ± 0.971 |
| 48.0 | 0.872 ± 0.681 | 1.53 ± 0.851 | 0.528 ± 0.831 |
| 72.0 | 0.300 ± 0.529 | 0.468 ± 0.650 | 0.00 ± 0.00 |

Table 14 provides the mean (±S.D.) pharmacokinetic parameters following dosing with MS Contin® And Example 3.

TABLE 14

Mean Pharmacokinetic Parameters ± Standard Deviation Following Administration of Each Formulation

| Parameter | Ex. 3 30 mg Fed | Ex. 3 30 mg Fasted | Ms Contin® 30 mg Fasted |
|---|---|---|---|
| $C_{max}$ (ng/ml) | 5.45 ± 1.68 | 4.03 ± 1.55 | 11.65 ± 4.82 |
| Tmax (hrs) | 8.04 ± 8.31 | 12.92 ± 14.66 | 2.77 ± 0.927 |
| AUC (0,72) (hr-ng/ml) | 118.12 ± 36.77 | 140.79 ± 51.23 | 114.05 ± 42.42 |

The ratios of least-squares mean AUC for the 30 mg capsules of Example 3 given under fed and fasted conditions indicate that AUC values under fed conditions are within ±20% of those under fasted conditions. The value of $C_{max}$ was 64% greater under fed conditions. The value of $T_{max}$ under fed conditions was approximately 50% of that when given under fasted conditions. The apparent absorption rate was approximately 35% greater under fed conditions, and the apparent elimination rate under fed conditions was approximately 35% of that under fasted conditions, indicating that absorption of morphine is slowed by the presence of food, and elimination rate is increased.

The ratios of least-squares mean AUC for the 30 mg capsule of Example 3 and the MS Contin® 30 mg tablet indicate that AUC (0,72) values for Example 3 are within ±20% of those for MS Contin®, and AUC (0,00) values are 44% greater for Example 3. The value of $C_{max}$ for Example 3 was 29.5% of that for MS Contin®. The value of $T_{max}$ under fed conditions was over five times that for Example 3. The apparent absorption rate was approximately 91% greater for Example 3, and the apparent elimination rate for Example 3 was over 16 times that for MS Contin®, indicating that absorption and elimination of morphine is slower for Example 3.

Linear regression of each pharmacodynamic parameter on the log-transformed concentrations for each subject and treatment resulted in 74 of 315 regressions (24%) having an $R^2$ value of 20% or higher, and 12 of 315 (4%) having a value of 50% or higher. When analyzed by treatment only, there were zero $R^2$ values higher than 10%. Of those individual $R^2$ values above 20%, 21 occurred in the 63 regressions (33%) of Subject's Modified Specific Drug Effect Questionnaire scores on log concentration, and 7 of the 63 (11%) were above 50%. These values indicate a possible linear relationship between the log concentrations and Subject's MSDEQ scores. Examination of the mean hysteresis curves also reveals a possible relationship between morphine concentration and Subject's MSDEQ scores. For each formulation, Subject Modified Specific Drug Effect Questionnaire scores tended to increase with an increase in morphine concentration, then decrease as morphine concentration decreased. No relationships were observed between morphine concentrations and any of the other pharmacodynamic parameters.

Figure 10:
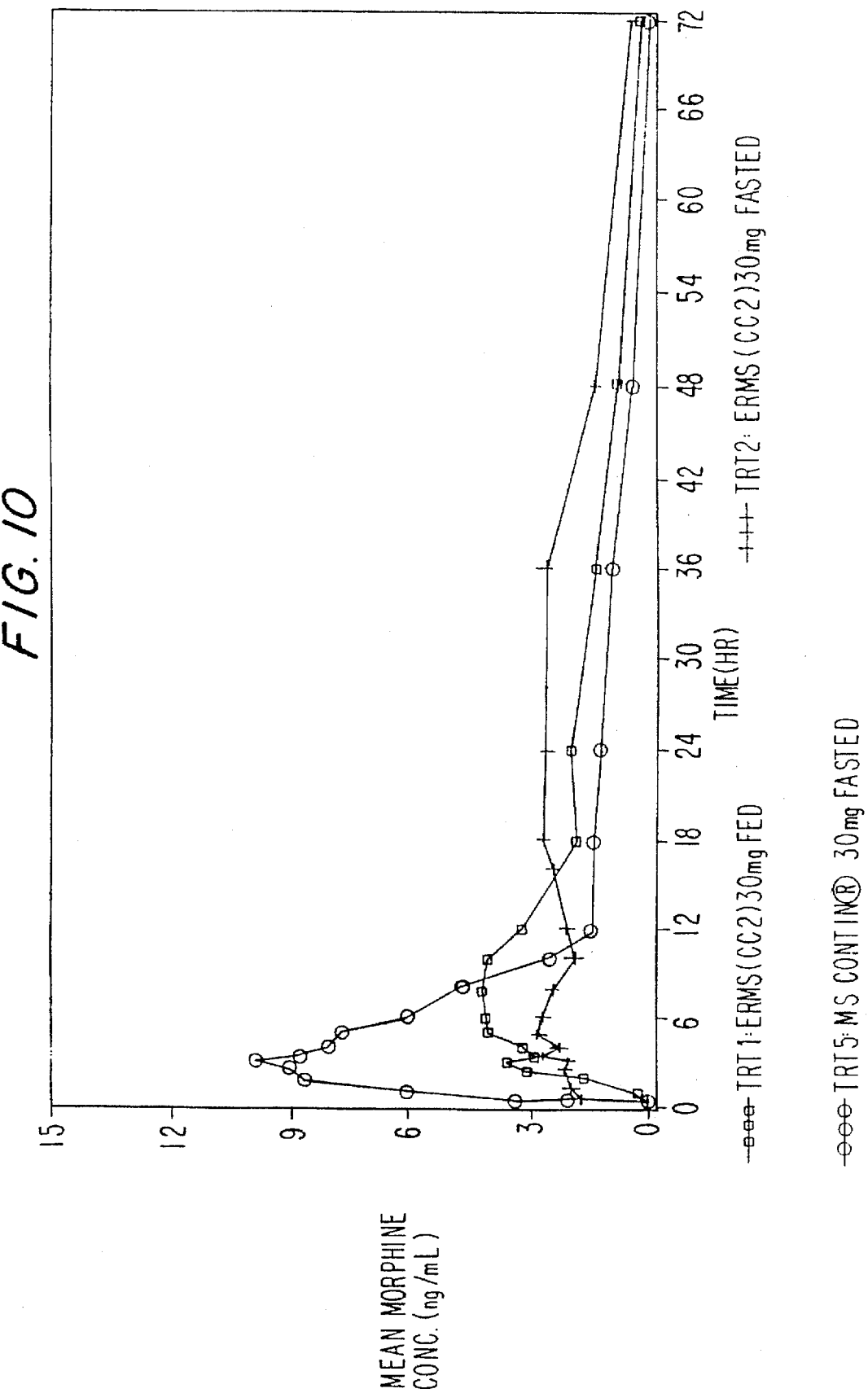
FIG. 10 is a graphical representation of the mean plasma morphine concentration-time profile obtained with the Comparative Example (MS Contin 30 mg) (fasted) as compared to the capsules of Example 3 (fed and fasted)
Figure 11:
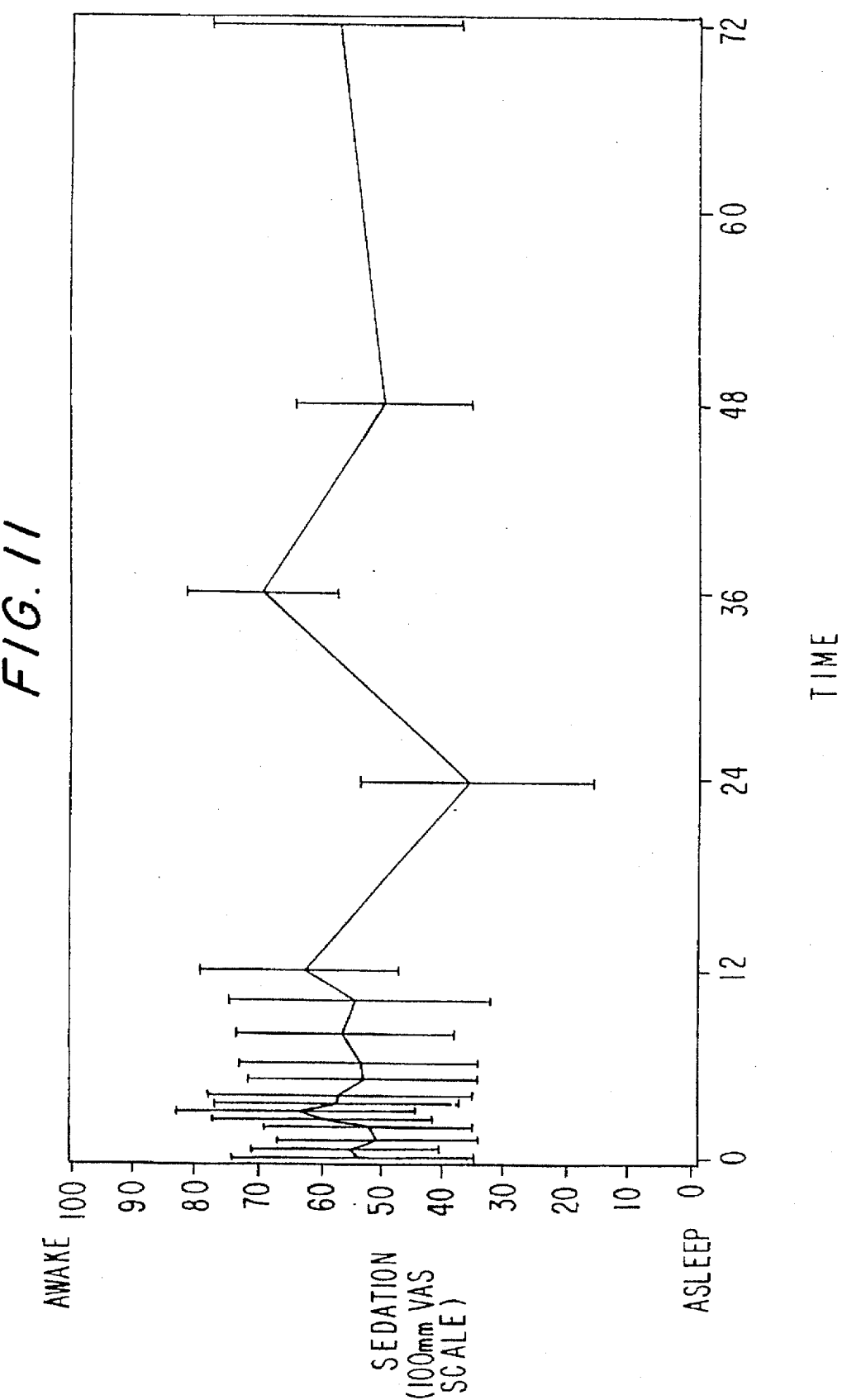
FIG. 11 is a graphical representation of the mean sedation vs. time curve for Example 3 (fasted)
Figure 12:
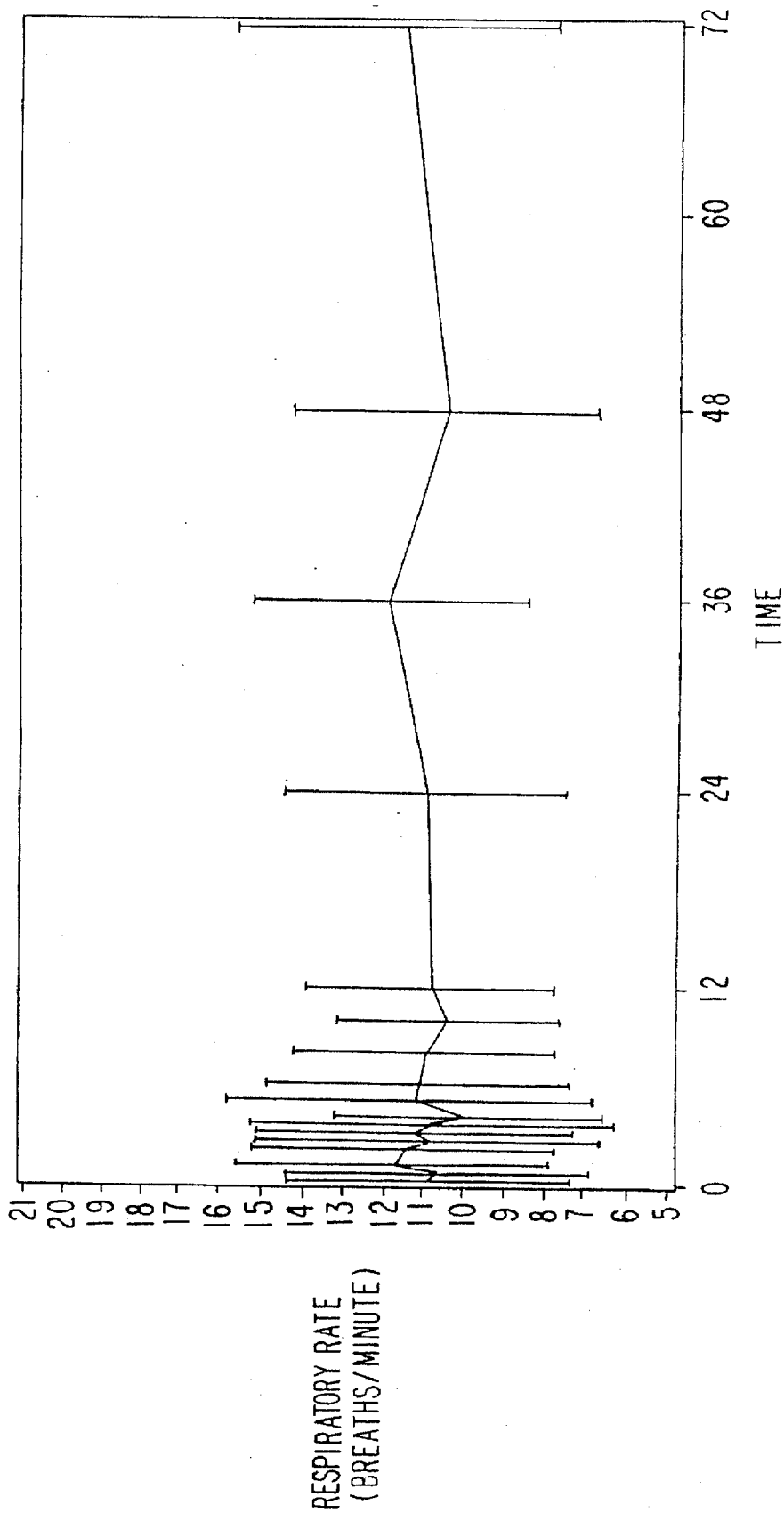
FIG. 12 is a graphical representation of the mean respiratory rate vs. time curve for Example 3 (fasted)
Figure 13:
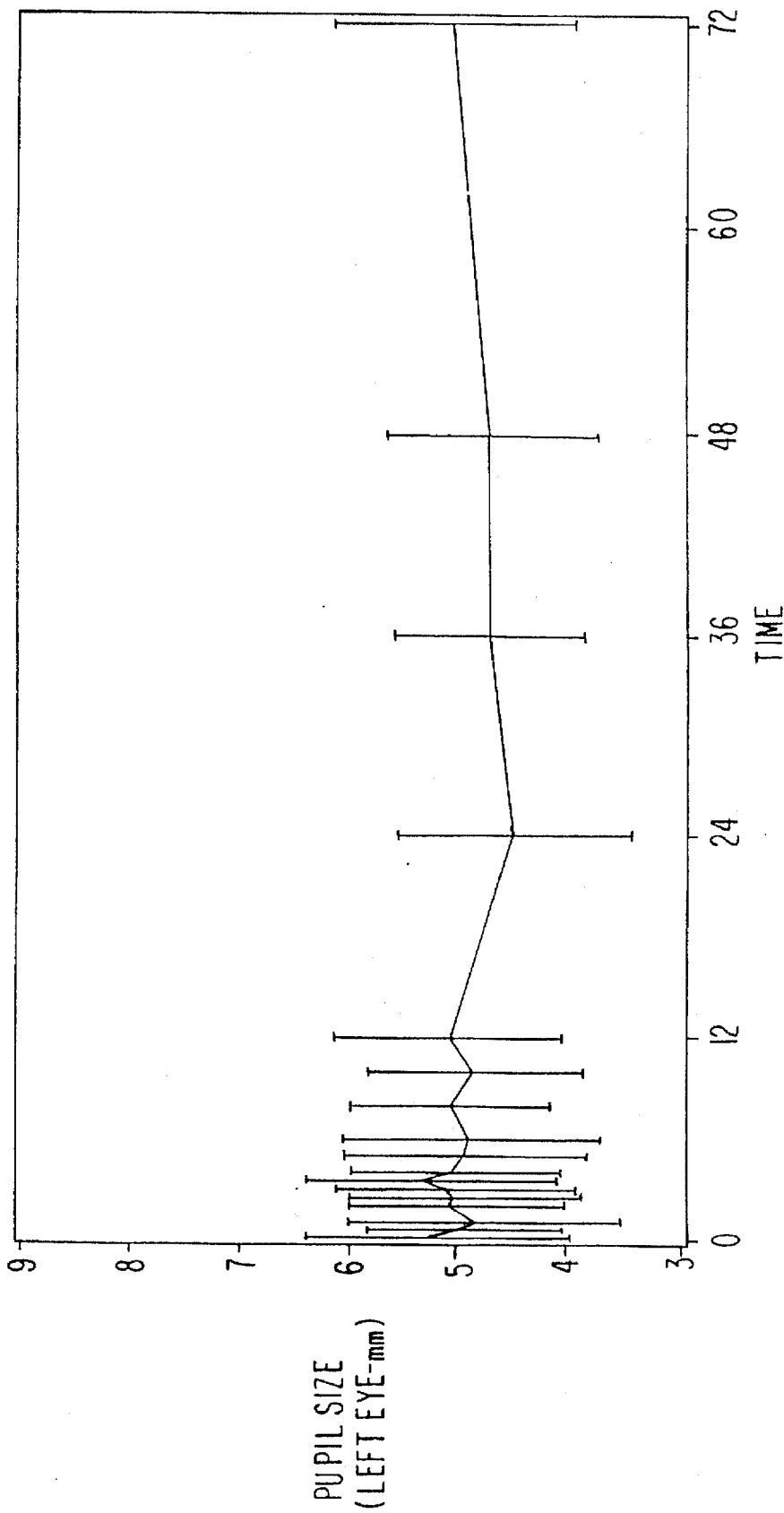
FIG. 13 is a graphical representation of the mean pupil size v. time curve for Example 3 (fasted)
Figure 14:
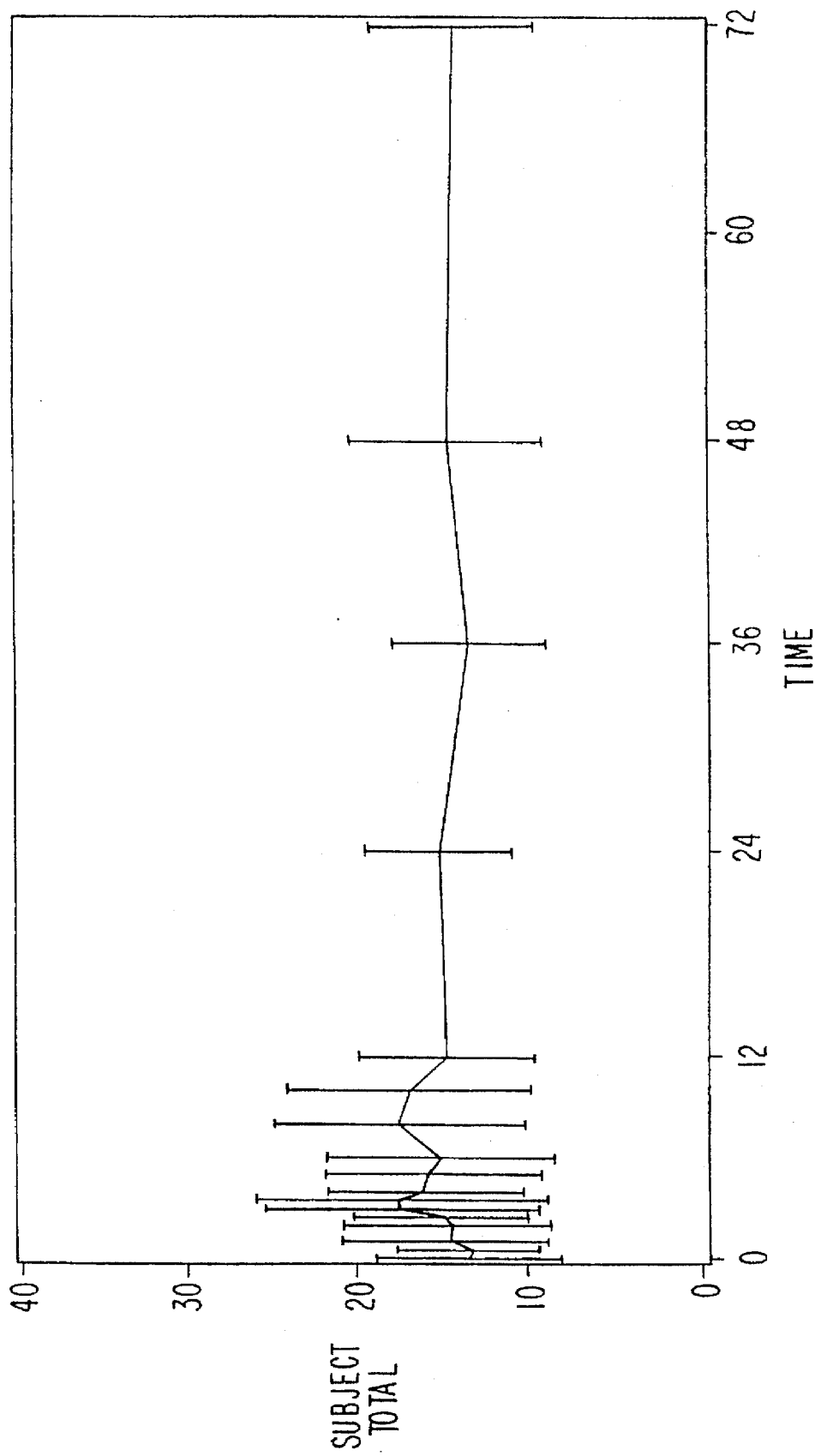
FIG. 14 is a graphical representation of the mean subject modified specific drug effect questionnaire vs. time curve for Example 2 (fasted).

FIG. 10 is a graphical representation of the mean plasma morphine concentration-time profile obtained with the Comparative Example (MS Contin 30 mg) (fasted) as compared to the capsules of Example 3 (fed and fasted). FIG. 11 is a graphical representation of the mean sedation vs. time curve for Example 3 (fasted). FIG. 12 is a graphical representation of the mean respiratory rate vs. time curve for Example 3 (fasted). FIG. 13 is a graphical representation of the mean pupil size v. time curve for Example 3 (fasted). FIG. 14 is a graphical representation of the mean subject modified specific drug effect questionnaire vs. time curve for Example 2 (fasted).

EXAMPLE 4

Beads with a higher loading of morphine sulfate were produced with the use of the powder layering technique in the Glatt Rotor Processor. The formulation of the high load beads is set forth in Table 15 below.

TABLE 15

| Ingredient | High Load Bead mg/unit | Percent (%) |
| --- | --- | --- |
| Morphine Sulfate Powder | 60.0 mg | 56.4% |
| Lactose | 12.0 mg | 11.3% |
| Eudragit RS30D | 4.16 mg | 3.9% |
| Povidone C-30 | 8.31 mg | 7.8% |
| Sugar Beads | 16.80 mg | 15.8% |
| Opadry | 5.06 mg | 4.8% |
| Purified Water | qs | — |
| Total | 106.33 mg | 100% |

These immediate release base beads were manufactured using the powder layering technique in the Glatt Rotor Processor.

The sustained release coating comprised an ethylcellulose acrylic polymer (i.e., Aquacoat ECD 30). A HPMC protective coat was also included after the Aquacoat layer to further enhance stability. The formula of the sustained-release coating of Example 1 is set forth in Table 16 below.

TABLE 16

| Ingredient | Amt/Unit (mg) | Percent (%) |
| --- | --- | --- |
| Morphine (high load) based beads | 106.33 mg | 73.1% |
| Retardant Coating | | |
| Aquacoat ECD 30 | 23.13 mg | 15.9% |
| Methocel E5 Premium | 3.46 mg | 2.4% |
| Triethyl Citrate | 5.32 mg | 3.6% |
| Purified Water | qs | — |
| Final Overcoat | | |
| Opadry Blue YS-1-10542A | 7.28 mg | 5.0% |
| Purified Water | qs | — |
| Total | 54.08 mg | 100.0% |

The sustained release coating and final overcoat were applied as follows: The combination of Aquacoat ECD 30 and Methocel E5 Premium was plasticized with triethyl citrate for approximately 30 minutes. A load of morphine sulfate beads was charged into a Wurster Insert of a Glatt equipped with a 1.2 mm spray nozzle and the beads are coated to a weight gain of 25%. Upon completion of the Retardant the beads were cured for 3 days in a Temperature/Humidity Chamber of 60° C./80% RH. The cured beads were then dried for 1 day in a dry oven of 60° C. The cured dried beads were charged into a Wurster Insert of a Glatt equipped with a 1.2 mm spray nozzle and the final protective Opadry dispersion overcoat was then applied. The finished sustained release beads along with the Low Load Immediate Release Morphine Sulfate beads were individually filled into the same gelatin capsules at a combined strength of 60 mg. The sustained released beads comprised 90% or 54 mg of strength and the Immediate Release Beads comprised 10% or 6 mg of the capsule strength.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and then placed into 900 ml of simulated intestinal fluid (without enzymes) after the first hour. The results of dissolution testing is set forth in Table 17 below.

TABLE 17

| Time | % Morphine Sulfate Dissolved |
| --- | --- |
| 1 hour | 10.4% |
| 2 hours | 11.4% |
| 4 hours | 17.5% |
| 8 hours | 31.8% |
| 12 hours | 54.0% |
| 18 hours | 88.6% |
| 24 hours | 102.3% |

EXAMPLE 5

Beads with a higher loading of morphine sulfate were produced with the use of the powder layering technique in the Glatt Rotor Processor. The formulation of the high load beads is set forth as per Table 18 in Example 5.

The sustained-release coating comprised an acrylic polymer (i.e., Eudragit® RS/RL). A HPMC protective coating was also included after the Eudragit layer to further enhance stability. The formula of the sustained-release coating of Example 5 is set forth in Table 18 below.

TABLE 18

| Ingredient | Amt/Unit (mg) | Percent (%) |
| --- | --- | --- |
| Morphine (high load) based beads | 106.33 mg | 87.96% |
| Retardant Coating | | |
| Eudragit RS 30 D | 5.05 mg | 4.18% |
| Eudragit RL 30 D | 0.27 mg | 0.22% |
| Triethyl Citrate | 1.06 mg | 0.88% |
| Talc | 2.13 mg | 1.76% |
| Final Overcoat | | |
| Opadry Blue YS-1-10542A | 6.04 mg | 5.0% |
| Purified Water | qs | — |
| Total | 120.88 mg | 100.0% |

The sustained-release and the final coatings were applied as follows. The Eudragit RS/RL 30D was plasticized with triethyl citrate and talc for approximately 30 minutes. A load of the morphine sulfate beads was charged into a Wurster Insert of a Glatt equipped with a 1.2 mm spray nozzle and the beads are coated to a weight gain of 5%. The final protective Opadry dispersion overcoat was then applied in the Wurster Insert. Upon completion the beads were cured for two days in a dry oven of 45° C. The cured beads were then filled into gelatin capsules at a 60 mg strength.

The capsules were then subjected to dissolution testing. Dissolution testing was conducted on the finished products via USP Apparatus II (Paddle Method). The capsules were placed into 700 ml of simulated gastric fluid (without enzymes) for the first hour at 100 rpm and 37° C., and then placed into 900 ml of simulated intestinal fluid (without enzymes) after the first hour. The results of dissolution testing is set forth in Table 19 below.

TABLE 19

| Time | % Morphine Sulfate Dissolved |
| --- | --- |
| 1 hour | 10.4% |
| 2 hours | 11.4% |
| 4 hours | 17.5% |
| 8 hours | 31.8% |
| 12 hours | 54.0% |

TABLE 19-continued

| Time | % Morphine Sulfate Dissolved |
|---|---|
| 18 hours | 88.6% |
| 24 hours | 102.3% |

EXAMPLE 6

Matrix Beads

Matrix Beads with a higher loading of morphine sulfate were produced with the use of the powder layering technique in the Glatt Rotor Processor. The formulation of the high load matrix beads is set forth in Table 20 below.

TABLE 20

| Ingredient | High Load Bead mg/unit | Percent (%) |
|---|---|---|
| Morphine Sulfate Powder | 60.0 mg | 46.0% |
| Lactose | 12.0 mg | 9.2% |
| Eudragit RS30D | 29.10 mg | 22.4% |
| Povidone C-30 | 5.80 mg | 4.5% |
| Sugar Beads | 16.80 mg | 12.9% |
| Opadry | 6.50 mg | 5.0% |
| Purified Water | qs | — |
| Total | 130.20 mg | 100% |

The matrix component is comprised of an ethylcellulose polymer (i.e., Aquacoat ECD 30). A HPMC protective coat was also included after the aquacoat layer to further enhance stability.

The matrix beads were made as follows. The Aquacoat ECD 30 was plasticized with tributyl citrate for approximately 30 minutes. Morphine sulfate powder and lactose were blended for approximately 5 minutes in a hobart mixer. A load of sugar beads was charged into the rotor insert of a Glatt equipped with a 1.2 mm spray nozzle/powder feed assembly. An Accurate Powder Feeder was positioned over the spray nozzle/powder feed assembly and charged with the morphine sulfate/lactose blend. The morphine sulfate/lactose blend is then layered onto the sugar beads using the plasticized hydrophobic polymer dispersion (i.e., Aquacoat ECD 30 and tributyl citrate) as the binding agent. Upon completion of the layering process the final protective opadry dispersion overcoat was then applied. The beads were then cured for one day in a dry oven of 60° C. The cured beads were then filled into gelatin capsules at a 60 mg strength.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and then placed into 900 ml of simulated intestinal fluid (without enzymes) after the first hour. The results of dissolution testing is set forth in Table 21 below.

TABLE 21

| Time | % Morphine Sulfate Dissolved |
|---|---|
| 1 hour | 32.4% |
| 2 hours | 44.8% |
| 4 hours | 59.6% |

TABLE 21-continued

| Time | % Morphine Sulfate Dissolved |
|---|---|
| 8 hours | 76.6% |
| 12 hours | 88.0% |
| 18 hours | 97.6% |
| 24 hours | 102.2% |

CLINICAL EVALUATION OF EXAMPLES 4, 5 AND 6

Fourteen normal healthy human subjects were enrolled in a six way crossover, randomized, open label study assessing the effect of food on the pharmacokinetics and pharmacodynamics of a single dose of either example 1, 2 or 3, with or without food. Plasma samples were analyzed for morphine levels and the following pharmacokinetic results were calculated, and the results are set forth in Table 22 below.

TABLE 22

| | Pharmacokinetic Parameter Per 60 mg Dose | | |
|---|---|---|---|
| Example Number | AUC (ng/ml.hr) | Cmax (ng/ml) | Tmax (hours) |
| 1 Fasted | 120 | 6.1 | 5.5 |
| 1 Fed | 131 | 8.3 | 8.8 |
| 2 Fasted | 149 | 11.3 | 6.7 |
| 2 Fed | 159 | 11.5 | 6.4 |
| 3 Fasted | 154 | 14.3 | 1.8 |
| 3 Fed | 154 | 12.7 | 2.8 |

EXAMPLE 7

Hydromorphone HCl 8 mg Once-a-Day Capsules

Drug Loading

Hydromorphone beads were prepared by dissolving hydromorphone HCl in water, adding Opadry Y-5-1442 and mixing for about 1 hour to obtain a 20% w/w suspension. This suspension was then sprayed onto Nu-Pareil 18/20 mesh beads using a Wurster insert.

First Overcoat

The loaded hydromorphone beads were then overcoated with a 5% w/w gain of Opadry Light Pink using a Wurster insert. This overcoat was applied as a protective coating.

Retardant Coat

After the first overcoat, the hydromorphone beads were then coated with a 5% weight gain of a retardant coating mixture of Eudragit RS 30D and Eudragit RL 30D at a ratio of 90:10, RS to RL. The addition of Triethyl Citrate (a plasticizer) and Talc (anti-tacking agent) was also included in the Eudragit suspension. The Wurster insert was used to apply the coating suspension.

Second Overcoat

Once the retardant coating was complete, the hydromorphone beads were given a final overcoat of Opadry Light Pink to a 5% weight gain using a Wurster insert. This overcoat was also applied as a protective coating.

Curing

After the completion of the final overcoat, the hydromorphone beads were cured in a 45° C. oven for 2 days.

Encapsulation

Beads were hand filled in size #2 clear gelatin capsules at all 8 mg strength of Hydromorphone HCl.

The formulation for Example 7 is set forth in Table 23 below:

TABLE 23

HYDROMORPRONE HCl 8 mg ONCE A DAY CAPSULES

| Ingredient | mg/Capsule |
|---|---|
| Loading | |
| Hydromorphone HCl | 8.00 |
| Opadry Light Pink (Y-5-1442) | 4.00 |
| Purified Water[1] | q.s. |
| 18/20 Mesh Sugar Spheres | 148.00 |
| Overcoating | |
| Opadry Light Pink (Y-5-1442) | 8.40 |
| Purified Water[1] | q.s. |
| Retardant Coating | |
| Eudragit RS 30D[2] | 7.60 |
| Eudragit RL 30D[2] | 0.80 |
| Triethyl Citrate | 1.68 |
| Talc | 3.36 |
| Purified Water[1] | q.s. |
| Second Overcoating | |
| Opadry Light Pink (Y-5-1442) | 9.60 |
| Purified Water[1] | q.s. |
| Encapsulation | n/a |
| Size #2 Clear Hard Gelatin Capsules | |
| Total Fill Weight | 191.44 mg |

[1]Used in processing and remains as residual moisture only.
[2]Dry weight.

Dissolution Testing.

The above capsules were tested using USP methodology and were found to have the following results set forth in table 24 below:

TABLE 24

| Time | Initial |
|---|---|
| 1 hour | 17.2 |
| 2 hours | 48.4 |
| 4 hours | 77.4 |
| 8 hours | 93.3 |
| 12 hours | 97.2 |
| 18 hours | 98.8 |
| 24 hours | 98.8 |

A single-dose randomized, crossover bioavailability study was conducted with the above 8 mg controlled release hydromorphone HCl capsules and two immediate release 4 mg tablets (Dilaudid®) as the reference in fed and fasted conditions. Blood samples were assayed for hydromorphone levels and the following pharmacokinetic parameters were calculated. The results are provided in Table 25 below:

TABLE 25

| Group | AUC (pg/ml/hr) | % IR | $T_{max}$ (hr) | $C_{max}$ (pg/ml) | $T_{1/2}$ (abs) |
|---|---|---|---|---|---|
| CR Fasted* | 21059 | 101 | 4.9 | 1259 | 2.56 |
| CR Fed* | 25833 | 106 | 4.6 | 1721 | 3.92 |
| IR Fasted** | 20903 | 100 | 0.85 | 3816 | 0.18 |
| IR Fed** | 24460 | 100 | 1.15 | 3766 | 0.32 |

*CR = Example 7
**IR = Dilaudid

The examples provided above are not meant to be exclusive. Many other variations of the present invention would be obvious to those skilled in the art, and are contemplated to be within the scope of the appended claims.

What is claimed is:

1. A method of effectively treating pain in humans, comprising orally administering to a human patient on a once-a-day basis an oral sustained release dosage form containing an opioid analgesic or salt thereof which upon administration provides a time to maximum plasma concentration ($T_{max}$) of said opioid in about 2 to about 10 hours and a maximum plasma concentration ($C_{max}$) which is more than twice the plasma level of said opioid at about 24 hours after administration of the dosage form, and which dosage form provides effective treatment of pain for about 24 hours or more after administration to the patient.

2. The method of claim 1, wherein the $T_{max}$ occurs in about 2 to about 8 hours after oral administration of said dosage form.

3. The method of claim 1, wherein the $T_{max}$ occurs in about 6 to about 8 hours after oral administration of said dosage form.

4. The method of claim 1, wherein said opioid analgesic is morphine sulfate.

5. The method of claim 1, wherein said dosage form contains from about 5 mg to about 800 mg morphine.

6. A method of effectively treating pain in a human patient, comprising orally administering to a human patient on a once-a-day basis an oral sustained release dosage form containing an opioid analgesic or salt thereof which provides a maximum plasma concentration ($C_{max}$) which is more than twice the plasma level of said opioid at about 24 hours after administration of the dosage form, and which provides effective treatment of pain for about 24 hours or more after administration to the patient.

7. The method of claim 6, wherein said opioid analgesic is morphine sulfate.

8. The method of claim 6, wherein said dosage form contains from about 5 mg to about 800 mg morphine.

9. A method of effectively treating pain in humans, comprising orally administering to a human patient on a once-a-day basis an oral sustained release dosage form containing an opioid analgesic or salt thereof which at steady-state provides a time to maximum plasma concentration ($T_{max}$) of said opioid in about 2 to about 10 hours and a maximum plasma concentration ($C_{max}$) which is more than twice the plasma level of said opioid at about 24 hours after administration of the dosage form, and which dosage form provides effective treatment of pain for about 24 hours or more after administration to the patient.

10. The method of claim 9, wherein the $T_{max}$ occurs from about 6 to about 8 hours after oral administration of said dosage form.

11. The method of claim 9, wherein said opioid analgesic is morphine sulfate.

12. A method of effectively treating pain in a human patient, comprising orally administering to a human patient on a once-a-day basis an oral sustained release dosage containing an opioid analgesic or salt thereof which at steady-state provides a maximum plasma concentration ($C_{max}$) which is more than twice the plasma level of said opioid at about 24 hours after administration of the dosage form, and which provides effective treatment of pain for about 24 hours or more after administration to the patient.

13. The method of claim 12, wherein said opioid analgesic is morphine sulfate.

14. The method of claim 12, wherein said dosage form contains from about 5 mg to about 800 mg morphine.

* * * * *